United States Patent
Yokoyama et al.

(10) Patent No.: US 10,053,437 B2
(45) Date of Patent: Aug. 21, 2018

(54) SALT OF DICARBOXYLIC ACID COMPOUND

(71) Applicant: Daiichi Sankyo Company, Limited, Tokyo (JP)

(72) Inventors: Mizuka Yokoyama, Tokyo (JP); Yasusi Ueda, Tokyo (JP); Daisuke Fukatsu, Hiratsuka (JP); Yuichi Aki, Hiratsuka (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/511,974

(22) PCT Filed: Sep. 18, 2015

(86) PCT No.: PCT/JP2015/076733
§ 371 (c)(1),
(2) Date: Mar. 16, 2017

(87) PCT Pub. No.: WO2016/047613
PCT Pub. Date: Mar. 31, 2016

(65) Prior Publication Data
US 2017/0291883 A1    Oct. 12, 2017

(30) Foreign Application Priority Data
Sep. 26, 2014  (JP) .................. 2014-196017

(51) Int. Cl.
| C07D 295/14 | (2006.01) |
| A61K 31/451 | (2006.01) |
| A61P 3/12 | (2006.01) |
| A61P 9/10 | (2006.01) |
| A61P 13/12 | (2006.01) |
| C07D 295/155 | (2006.01) |

(52) U.S. Cl.
CPC ...... *C07D 295/155* (2013.01); *C07B 2200/13* (2013.01)

(58) Field of Classification Search
CPC .................................................. C07D 295/155
USPC .......................................................... 514/331
See application file for complete search history.

(56) References Cited

U.S. PATENT DOCUMENTS

| 5,071,841 | A | 12/1991 | Sohda et al. |
| 9,617,232 | B2 * | 4/2017 | Uto ...................... C07D 213/75 |
| 9,670,173 | B2 * | 6/2017 | Uto ...................... C07D 213/75 |
| 2006/0217426 | A1 | 9/2006 | Eto et al. |
| 2011/0130445 | A1 | 6/2011 | Lampe et al. |

(Continued)

FOREIGN PATENT DOCUMENTS

| CN | 1045106 A | 9/1990 |
| CN | 1210856 A | 3/1999 |

(Continued)

OTHER PUBLICATIONS

Morissette; Advanced Drug Delivery Reviews 2004, 56, 275-300.*

(Continued)

*Primary Examiner* — Daniel R Carcanague
(74) *Attorney, Agent, or Firm* — Foley & Lardner LLP

(57) ABSTRACT

It is an object of the present invention to provide a medicament for preventing or treating hyperphosphatemia. The solution is crystals, or hydrate thereof, of a salt of a compound represented by formula (I).

13 Claims, 8 Drawing Sheets

(56) References Cited

U.S. PATENT DOCUMENTS

| | | | |
|---|---|---|---|
| 2013/0029973 A1 | 1/2013 | Hachiya et al. | |
| 2013/0053369 A1 | 2/2013 | Hachiya et al. | |
| 2013/0336920 A1 | 12/2013 | Lewis et al. | |
| 2014/0023611 A1 | 8/2014 | Lindeman et al. | |
| 2015/0031727 A1 | 1/2015 | Miura et al. | |
| 2016/0046568 A1* | 2/2016 | Uto .................. | C07D 213/75 514/331 |
| 2017/0015641 A1* | 1/2017 | Uto .................. | C07D 213/75 |

FOREIGN PATENT DOCUMENTS

| | | |
|---|---|---|
| CN | 102712577 A | 10/2012 |
| CN | 102869656 A | 1/2013 |
| EP | 0 376 197 A1 | 7/1990 |
| EP | 0 899 262 A2 | 3/1999 |
| EP | 2 565 190 A1 | 3/2013 |
| JP | 2013-509369 A | 3/2013 |
| WO | WO-2009/157418 A1 | 12/2009 |
| WO | WO-2011/051165 A1 | 5/2011 |
| WO | WO-2011/136269 A1 | 11/2011 |
| WO | WO-2012/006475 A1 | 1/2012 |
| WO | WO-2013/082751 | 6/2013 |
| WO | WO-2013/082756 | 6/2013 |
| WO | WO-2014/003153 A1 | 1/2014 |
| WO | WO-2014/175317 A1 | 10/2014 |
| WO | WO-2016/047613 | 3/2016 |
| WO | WO2016171240 * | 10/2016 |

OTHER PUBLICATIONS

Columbian Office Action issued in application No. 15.251845 dated Dec. 2, 2015.

F. Malberti, "Hyperphosphataemia: Treatmeat Options," Drugs 73:673-688 (2013).

F. Verbeke et al., "Prognostic Value of Aortic Stiffness and Calcification for Cardiovascular Events and Mortality in Dialysis Patients: Outcome of the Calcification Outcome in Renal Disease (CORD)Study," Clinical Journal of the American Society of Nephrology vol. 6, Jan. 2011 153-159.

First Office Action issued in Chinese Patent Application No. 201480022830.2 dated May 10, 2016.

H. Murer, et al. "The Sodium Phosphate Cotransporter Family SLC34," Pflugers Arch-Eur J Physiol (2004) 447: 763-767.

International Search Report issued in corresponding application No. PCT/JP2014/061390 dated Jul. 15, 2014.

International Search Report issued in corresponding application No. PCT/JP2015/076733 dated Nov. 17, 2015.

M.R. Wills et al., "Aluminum Poisoning: Dialysis Encephalopathy, Osteomalacia, and Anaemia," The Lancet, Jul. 2, 1983, 29-34.

N. Eto et al., "Nicotinamide prevents the development of hyperphosphataemia by suppressing intestinal sodium-dependent phosphate transporter in rats with adenine-induced renal failure," Nephrol. Dial. Transplant 20:1378-1384 (2005).

S. C. Schiavi et al., "Npt2b Deletion Attenuates Hyperphosphatemia Associated with CKD," J Am Soc Nephrol 23: 1691-1700, 2012.

T. Kakuta et al., "Effect of Sevelamer and Calcium-Based Phosphate Binders on Coronary Artery Calcification and Accumulation of Circulating Advanced Glycation End Products in Hemodialysis Patients," Am J Kidney Dis. 2011; 57(3): 422-431.

T. Maruyama et al., "To Facilitate the Compliance of Phosphate Binder for the Control of Hyperphosphatemia in Chronic Kidney Disease Patients," Clinical Calcium vol. 19, No. 2, 2009, 100 (248).

U.S. Notice of Allowance on U.S. Appl. No. 14/784,187 dated Feb. 2, 2017.

U.S. Notice of Allowance on U.S. Appl. No. 15/282,384 dated Mar. 29, 2017.

U.S. Office Action on U.S. Appl. No. 14/784,187 dated Sep. 14, 2016.

U.S. Office Action on U.S. Appl. No. 15/282,384 dated Nov. 4, 2016.

Y. Sabbagh et al., "Intestinal Npt2b Plays a Major Role in Phosphate Absorption and Homeostasis," J. Am. Soc. Nephrol. 20:2348-2358 (2009).

Extended European Search Report dated Feb. 12, 2018 in corresponding application No. 15845095.7.

* cited by examiner

SALT OF DICARBOXYLIC ACID COMPOUND

CROSS-REFERENCE TO RELATED APPLICATIONS

This application is a U.S. National Stage Application of International Patent Application No. PCT/JP2015/076733, filed on Sep. 18, 2015, which claims benefit to Japanese Patent Application No. 2014-196017, filed Sep. 26, 2014, the entireties of which are incorporated herein by reference.

TECHNICAL FIELD

The present invention relates to crystals of a salt, or hydrate thereof, of a compound that is useful for preventing or treating hyperphosphatemia or a disease associated with hyperphosphatemia.

BACKGROUND ART

Phosphorus is present in a living body in various forms as constitutional elements important for the body, such as DNA, RNA or bone, and plays an important role in life-sustaining activities.

Phosphoric acid is mainly absorbed from food through the digestive tract in the form of inorganic phosphorus, and it is then eliminated through the kidney in the form of urine (Non Patent Literature 1).

Absorption of phosphorus through the digestive tract, elimination thereof through the kidney, and absorption and/or metabolism thereof from the bone are controlled by the action of vitamin D, parathyroid hormone (PTH), etc., and thus, the blood level of phosphorus is maintained constant.

In the case of renal failure, hyperphosphatemia in which the blood level of phosphorus shows an extremely high value is developed in many cases due to a reduction in elimination of phosphoric acid from the kidney. An excessive amount of phosphoric acid binds to blood calcium, and it causes ectopic calcification in the cardiovascular system, so that it seems to become a risk factor for cardiovascular diseases such as myocardial infarction (Non Patent Literature 2).

Moreover, hyperphosphatemia secondarily causes hypocalcemia, and in compensation, hyperparathyroidism characterized by an increase in the blood. PTH level is developed. This also becomes a main factor for developing renal osteodystrophy. As mentioned above, hyperphosphatemia in chronic renal failure patients reduces the QOL of the patients due to bone fracture, bone pain, etc., and at the same time, it becomes a main factor for the death of chronic renal failure patients.

At present, as a therapeutic drug for hyperphosphatemia, there is used a phosphate adsorbent that adsorbs phosphoric acid in the digestive tract and thereby suppresses the absorption thereof, as well as diet restriction. As oral adsorbents, various medicaments such as calcium preparations (precipitated calcium carbonate, etc.), polymer preparations (sevelamer hydrochloride), and metallic salt preparations (aluminum hydroxide and lanthanum carbonate) have been used. It is pointed out that individual preparations have problems.

Regarding the calcium preparations, it has been demonstrated that vascular calcification is promoted due to hypercalcemia (Non Patent Literature 3), and the polymer preparations are problematic in terms of drug compliance caused by administration at a dose of several grams per day and digestive symptoms such as constipation and/or diarrhea (Non Patent Literature 4).

Moreover, regarding the metallic salt preparations, the risk of accumulation in the body is pointed out (Non Patent Literature 5). Thus, adequate therapeutic drugs for hyperphosphatemia have not yet been developed.

It has been reported that a sodium-dependent phosphate transporter expressed in small intestinal epithelial cells plays an important role in absorption of inorganic phosphate through the digestive tract (Non Patent Literature 6). It is anticipated that a compound that specifically inhibits the active transport of phosphate can suppress absorption of phosphorus through the digestive tract, more efficiently than oral adsorbents, and that it can improve the drug comp lance that has been the problem of oral adsorbents and can solve problems such as digestive symptoms and accumulation.

Under the aforementioned circumstances, it has been desired to develop a novel drug for preventing or treating hyperphosphatemia or a disease associated with hyperphosphatemia.

The compound described in WO2011/136269 is relevant to the compound of the present invention.

CITATION LIST

Patent Literature

Patent Literature 1: WO2011/136269

Non Patent Literature

Non Patent Literature 1: H. Murer et al., Pflugers Arch—Eur J Physiol (2004) 447: 763-767
Non Patent Literature 2: F. Verbeke et al., Clinical Journal of the American Society of Nephrology 6, 153 (2011)
Non Patent Literature 3: T. Kakuta et al., Am J Kidney Dis. 57(3): 422 (2011)
Non Patent Literature 4: T. Maruyama et al., CLINICAL CALCIUM 19, 2, 100(248), (2009)
Non Patent Literature 5: M. R. Wills, J. Savory J. Lancet 2, 29 (1983)
Non Patent Literature 6: S. C. Schiavi et al., J Am Soc Nephrol 23: 1691, 2012

SUMMARY OF INVENTION

Technical Problem

It is an object of the present invention to provide crystals of a salt, or hydrate thereof, of a compound that is useful as an active ingredient for preventing and treating hyperphosphatemia. Since the crystals of the salt, or hydrate thereof, of the compound of the present invention have low hygroscopicity and are excellent in physical and/or chemical stability, they are useful.

Solution to Problem

The present inventors have conducted intensive studies directed towards developing a compound useful as an active ingredient for preventing and treating hyperphosphatemia. As a result, the inventors have discovered the salt, or hydrate thereof, of the compound of the present invention, and crystals thereof which have low hygroscopicity and are excellent in physical and/or chemical stability. Specifically, the present invention is as described below.

[1]
Crystals of a salt, or hydrate thereof, of a compound represented by formula (I):

[Formula 1]

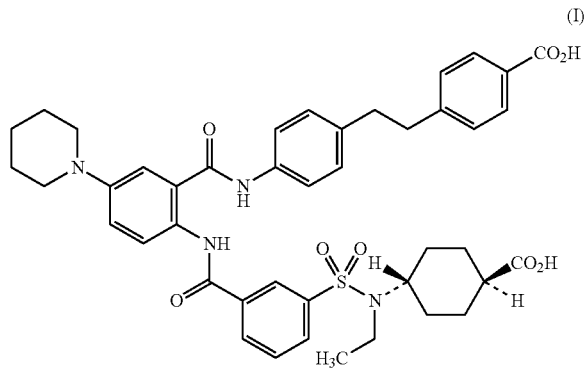

[2]
The crystals of a salt, or hydrate thereof, of a compound according to [1] above, wherein the salt is a disodium salt.
[3]
The crystals of a salt, or hydrate thereof, of a compound according to [1] or [2] above, wherein the hydrate is a trihydrate.
[4]
Crystals of a disodium salt trihydrate of the compound represented by formula (I).

[Formula 2]

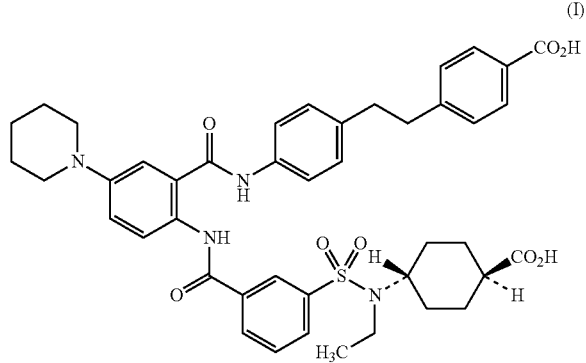

[5]
The crystals according to [4] above, wherein, in powder X-ray diffractometry using Cu as a radiation source, 2θ(°) shows peaks at around 5.72, around 10.10, around 10.96, around 11.98, around 13.34, around 15.02, around 17.26, around 20.26, around 21.66, and around 22.36 (α crystals).
[6]
The crystals according to [2.] above, wherein, in powder X-ray diffractometry using Cu as a radiation source, 2θ(°) shows peaks at around 5.82, around 9.78, around 11.18, around 12.26, around 12.86, around 15.38, around 16.34, around 18.34, around 19.68, and around 22.54 (β crystals).
[7]
The crystals according to [2] above, wherein, in powder X-ray diffractometry using Cu as a radiation source, 2θ(°) shows peaks at around 5.82, around 9.78, around 11.18, around 12.26, around 12.86, around 15.38, around 16.34, around 18.34, around 19.68, and around 22.54 (γ crystals).
[8]
The crystals according to [2] above, wherein, in powder X-ray diffractometry using Cu as a radiation source, 2θ(°) shows a peak only at around 6.04 (δ crystals).
[9]
A pharmaceutical composition comprising the crystal according to any one selected from [1] to [8] above.
[10]
The pharmaceutical composition according to [9] above, which is used as a phosphorus uptake inhibitor.
[11]
The pharmaceutical composition according to [9] above, which is used to prevent or treat hyperphosphatemia.
[12]
Use of the crystals according to any one of [1] to [8] above for the production of a pharmaceutical composition for preventing or treating hyperphosphatemia.
[13]
The crystals according to any one of [1] to [8] above for use in preventing or treating hyperphosphatemia.
[14]
A method for preventing or treating hyperphosphatemia, which comprises administration of an effective amount of the crystals according to any one of [1] to [8] above.

Advantageous Effects of Invention

Since the crystals of the salt, or hydrate thereof, of the compound of the present invention have extremely low hygroscopicity, they have properties that are advantageous in formulation of pharmaceutical products. In addition, since the crystals of the salt, or hydrate thereof, of the compound of the present invention are excellent in solubility and also have excellent physical stability and chemical stability, they have properties that are advantageous in formulation of pharmaceutical products.

The crystals of the salt, or hydrate thereof, of the compound of the present invention, which have low hygroscopicity, are excellent in preservation properties, and easy to control in terms of their quality. Moreover, even in the case where a preparation is formed using the crystals of the salt, or hydrate thereof, of the compound of the present invention, they contribute to stabilization of the preparation because of their low hygroscopicity, excellent physical stability and chemical stability, and the like. Thus, by using the crystals of the salt, or hydrate thereof, of the compound of the present invention, pharmaceutical products with higher quality can be provided.

DESCRIPTION OF EMBODIMENTS

Figure 1:
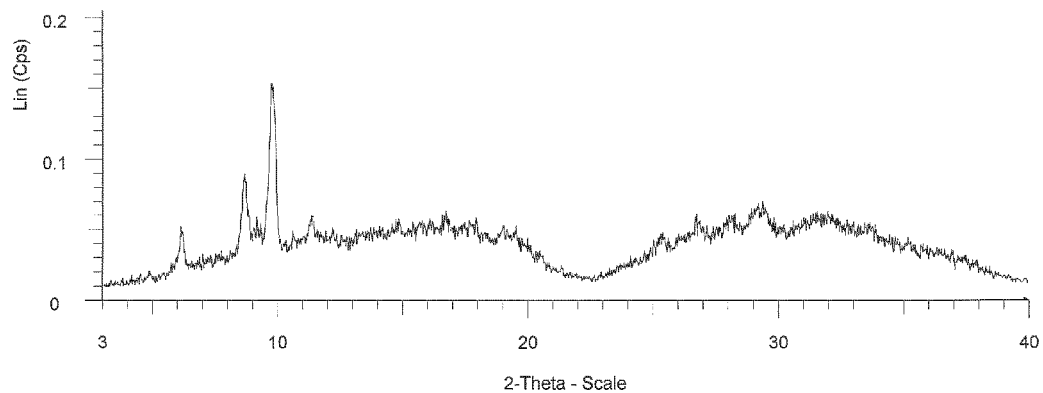
FIG. 1 is a view showing the powder X-ray diffraction pattern of Example 1 (a mixture of α crystals and a ε crystals).

Since the crystals of the salt, or hydrate thereof, of the compound of the present invention have extremely low hygroscopicity, they have properties that are advantageous in formulation of pharmaceutical products. In addition, since the crystals of the salt, or hydrate thereof, of the compound of the present invention are excellent in solubility and also have excellent physical stability and chemical stability, they have properties that are advantageous in formulation of pharmaceutical products, thereby providing pharmaceutical products with higher quality.

Hereinafter, the present invention will be described in detail.

With regard to powder X-ray diffraction patterns, diffraction angles and the overall pattern are important to recognize the identity of crystals because of the properties of the data, and relative intensities may fluctuate somewhat depending on the direction of crystal growth, particle size, and measurement conditions.

The crystals of the present invention include several types of crystals. In the present invention, there is not only the case where a single type of crystal is present, but also the case where several types of crystal are present together. Such a mixture of crystals is also included in the present invention.

There may be cases where the numerical values obtained from various types of patterns may generate some errors, depending on the direction of crystal growth, the particle size, and measurement conditions. Accordingly, in the present description, the term "around" used to indicate the value of a diffraction angle (2θ) in a powder X-ray diffraction pattern means that the diffraction angle (2θ) is indicated as an approximate value, and that the diffraction angle is preferably in the range of 0.2(°) below and above the approximate value, and more preferably in the range of 0.1(°) below and above the approximate value.

Moreover, the term "around" used to indicate the value of an endothermic peak in a thermogravimetry-differential thermal analysis (TG-DTA) means that the endothermic peak is indicated as an approximate value, and that the endothermic peak is preferably in the range of 2(° C.) below and above the approximate value, and more preferably in the range of 1(° C.) below and above the approximate value.

(Production Method)

Hereafter, production methods will be described. However, the methods for producing crystals of a salt, or hydrate thereof, of a compound are not limited to the following methods.

[Method A]

Method A is a method for producing the compound (A-3).

Method A

[Formula 3]

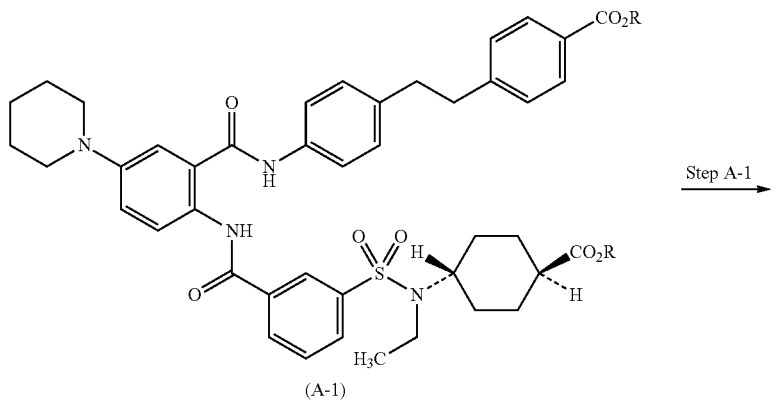

Step A-1

(A-1)

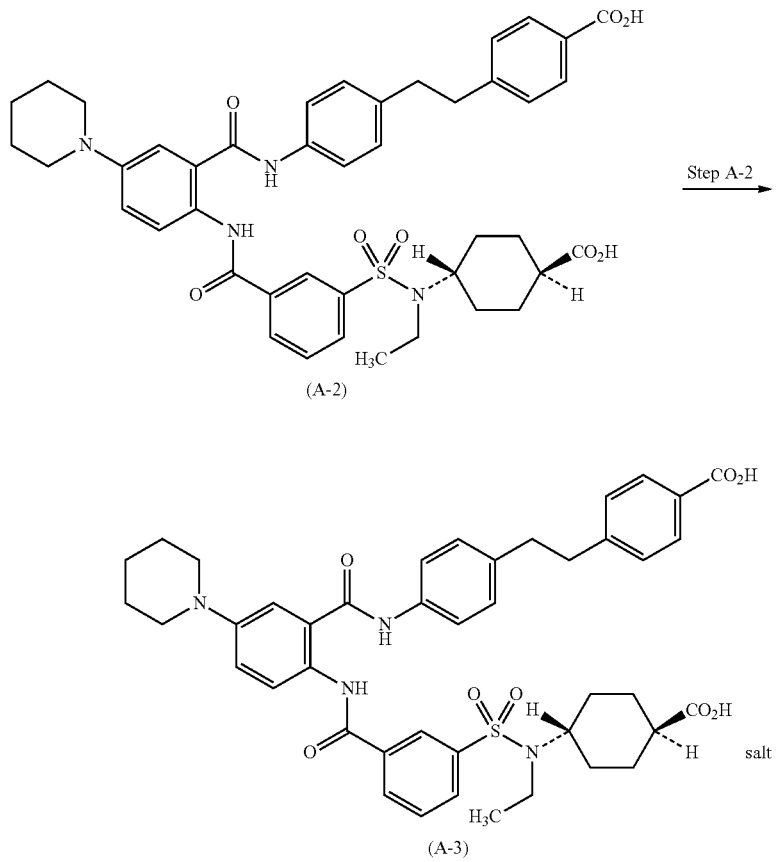

wherein
R represents a linear or branched alkyl group containing 1 to 6 carbon atoms, and preferably represents a methyl group, an ethyl group, a propyl group or an isopropyl group.

The "salt" represents a salt with an inorganic or organic base that forms a salt with a carboxy group, and/or a salt with an inorganic or organic acid that forms a salt with an amino group.

In the case of the salt with an inorganic or organic base that forms a salt with a carboxy group,
preferred examples of the salt include: alkali metal salts such as a sodium salt, a potassium salt, or a lithium salt; alkaline-earth metal salts such as a magnesium salt or a calcium salt; organic base salts such as an N-methylmorpholine salt, a triethylamine salt, a tributylamine salt, a diisopropylethylamine salt, a dicyclohexylamine salt, an N-methylpiperidine salt, a pyridine salt, a 4-pyrrolidinopyridine salt, a piperazine salt, or a picoline salt; and amino acid salts such as a glycine salt, a lysine salt, an arginine salt, an ornithine salt, a glutamate, or an aspartate, and
more preferred examples of the salt include a sodium salt, a potassium salt, and a piperazine salt.

In the case of the salt with an inorganic or organic acid that forms a salt with an amino group,
preferred examples of the salt include: inorganic acid salts such as hydrohalides including a hydrofluoride, a hydrochloride, a hydrobromide or a hydroiodide, nitrates, perchlorates, sulfates, or phosphates; and organic acid salts, such as lower alkanesulfonates including methanesulfonate, trifluoromethanesulfonate, or ethanesulfonate, arylsulfonates including benzenesulfonate or p-toluenesulfonate, acetates, malates, fumarates, succinates, citrates, ascorbates, tartrates, oxalates, or maleates, and
a more preferred example of the salt is p-toluenesulfonate.

(Step A-1) Step of Hydrolyzing Ester

This is a step of hydrolyzing an ester of the compound (A-1) in the presence of a base in a solvent to obtain the compound (A-2).

Preferred examples of the base used herein include alkali metal hydroxides such as sodium hydroxide or lithium hydroxide. A preferred example of the solvent used herein is a mixed solvent of water and tetrahydrofuran/methanol.

The reaction temperature is generally approximately 20° C. to 60° C., and the reaction time is generally approximately 1 to 10 hours.

(Step A-2) Step of Converting Carboxylic Acid into Salt

This is a step of treating the compound (A-2) with an alkali metal alkoxide such as potassium t-butoxide to convert it into a salt to obtain the compound (A-3). By the same method, various inorganic and organic salts and also their hydrates can be produced.

For example, the compound (A-2) is dissolved in a solution such as tetrahydrofuran, and potassium t-butoxide is then added to the solution at a temperature of approximately 0° C. to 40° C., so that the compound is converted into a salt, thereby obtaining a potassium salt.

[Method B]

Method B is a method for producing a compound (B-3) that corresponds to the compound (A-1) used in Method A.

Method B

[Formula 4]

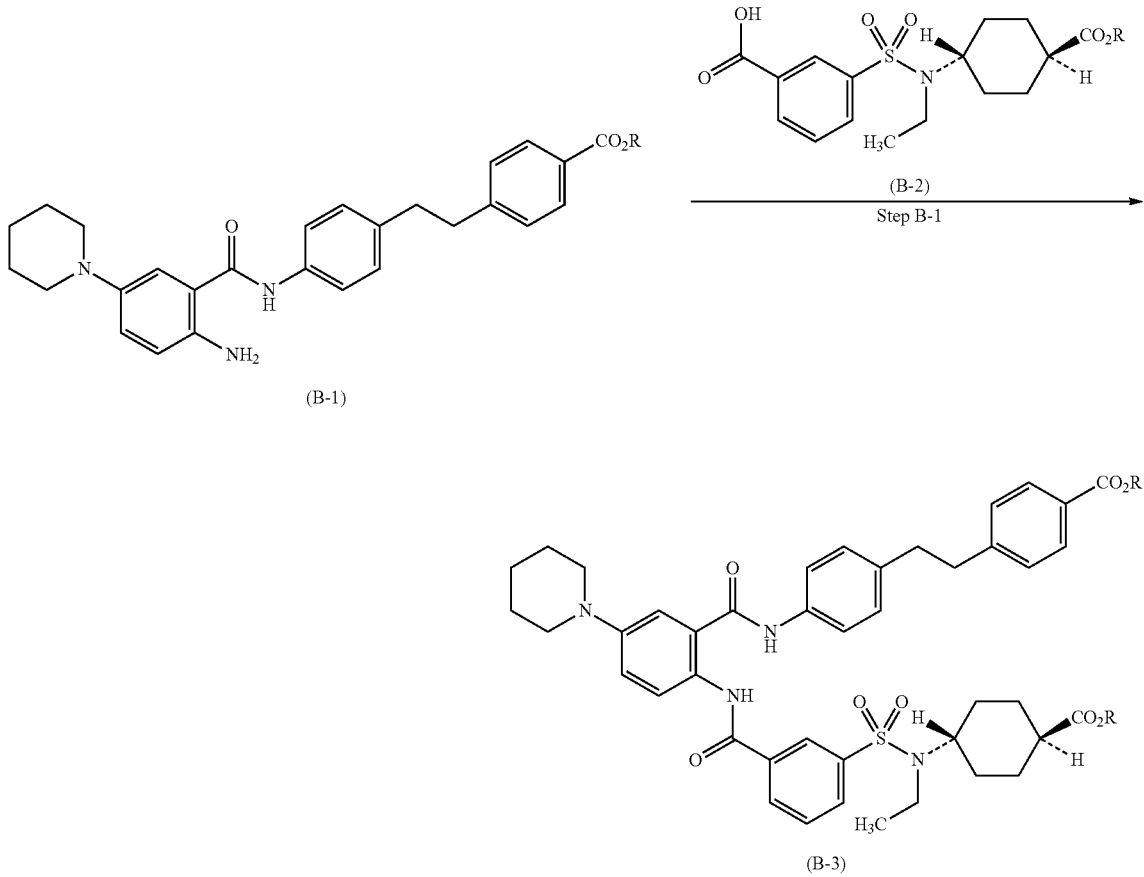

wherein R represents a linear or branched alkyl group containing 1 to 6 carbon atoms, and preferably represents a methyl group, an ethyl group, a propyl group or an isopropyl group.

(Step B-1) Step of Forming Amide by Condensation

This is a step of producing the compound (B-3) by (i) allowing the carboxylic acid of the compound (B-2) to react with oxalyl chloride to activate it and then allowing the resulting compound to react with the compound (B-1), or by (ii) allowing the compound (B-2) to react with the compound (B-1) in the presence of a condensation agent.

In the case of (i), for example, oxalyl chloride and a small amount of dimethylformamide are added into a solution of the compound (B-2) in methylene chloride at a temperature of 0° C. to room temperature, and the obtained mixture is then left for a while, and thereafter, the compound (B-1) and a base such as pyridine are added to the reaction solution at a temperature of 0° C. to room temperature. In general, the reaction temperature is set at approximately room temperature to approximately 80° C., and the reaction time is set at approximately 1 to 24 hours.

In the case of (ii), for example, a base and a condensation agent are added to a solution of the compound (B-1) and the compound (B-2) in dimethylformamide or methylene chloride, and a reaction is then carried out. In general, the reaction temperature is approximately room temperature to approximately 80° C., and the reaction time is approximately 1 to 24 hours.

As a base used herein, a tertiary amine such as diisopropylethylamine is preferable.

Examples of the condensation agent used herein include:

1-[bis(dimethylamino)methylene]-1H-benzotriazolium-3-oxide hexafluorophosphate (hereinafter also referred to as "HBTU"), 2-(1H-7-azabenzotriazol-1-yl)-1,1,3,3-tetramethyluronium hexafluorophosphate (hereinafter also referred to as "HATU"), 4-(4,6-dimethoxy-1,3,5-triazin-2-yl)-4-methylmorpholinium chloride n-hydrate (hereinafter also referred to as "DMT-MM"), and 1-ethyl-3-(3-dimethylaminopropyl)carbodiimide hydrochloride (hereinafter also referred to as "WSC" or "EDCI").

[Method C]

Method C is a method for producing a compound (C-2) that corresponds to the compound (B-1) used in Method B.

Method C

[Formula 5]

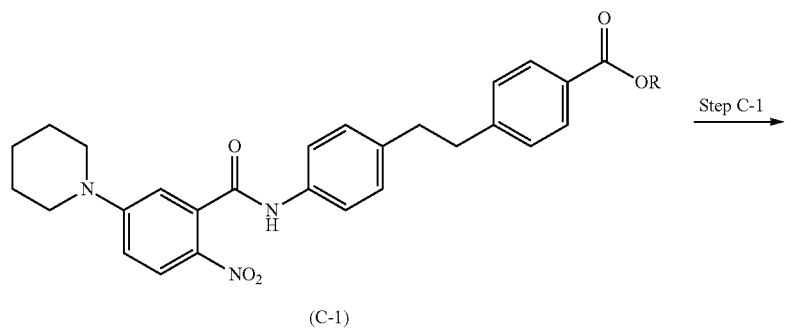

(C-1)

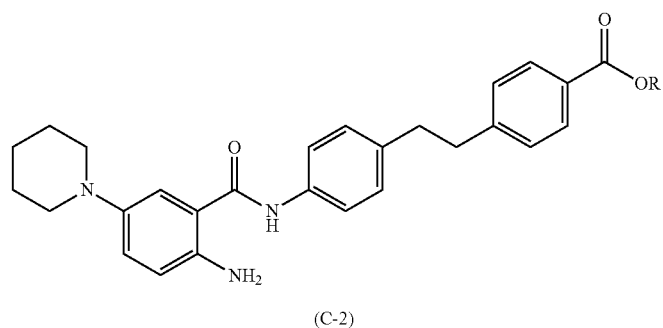

(C-2)

wherein R represents a linear or branched alkyl group containing 1 to 6 carbon atoms, and preferably represents a methyl group, an ethyl group, a propyl group or an isopropyl group.

(Step C-1) Step of Reducing Nitro Group to Form Amino Group

This is a step of reacting a solution of the compound (C-1) under a hydrogen atmosphere in the presence of a metal catalyst such as 10% palladium on carbon.

Preferred examples of the solvent used herein include ethers such as tetrahydrofuran, alcohols such as ethanol, and a mixed solvent of tetrahydrofuran/ethanol.

In general, the reaction temperature is approximately room temperature to approximately 60° C., and the reaction time is approximately 1 to 10 hours.

In addition, the present step can also be carried out by performing the reduction reaction using iron powder and ammonium chloride by heating them to reflux in an ethanol/water solvent.

[Method D]

Method D is a method for producing a compound (D-4) that corresponds to the compound (C-1) used in Method C.

Method D

[Formula 6]

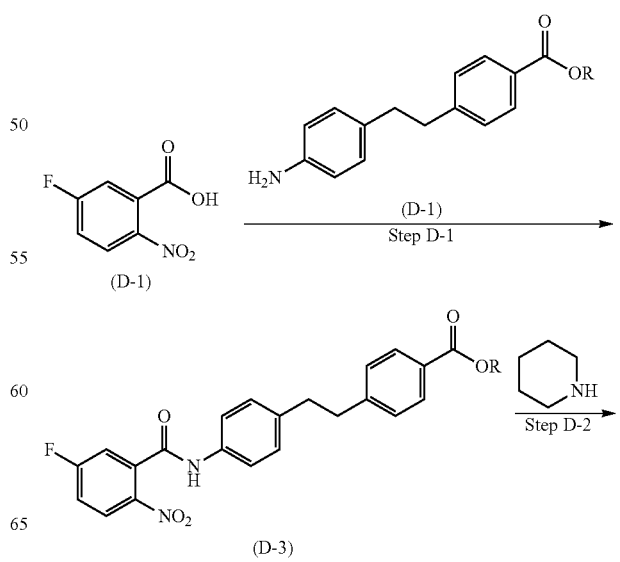

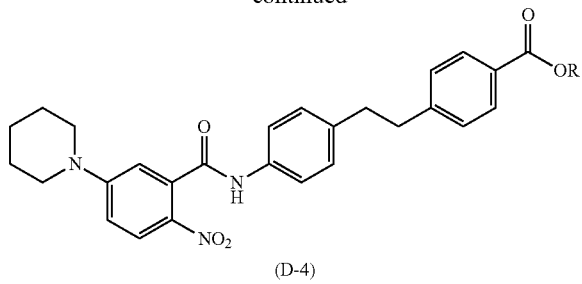

(D-4)

wherein R represents a linear or branched alkyl group containing 1 to 6 carbon atoms, and preferably represents a methyl group, an ethyl group, a propyl group or an isopropyl group.

(Step D-1) Step of Forming Amide by Condensation.

This is a step of producing an amide under the same conditions as those in Step B-1 of Method B.

(Step D-2) Step of Introducing Substituent on Benzene Ring by Substitution Reaction.

This is a step of adding piperidine to a solution of the compound (D-3), and then performing a reaction.

As a solvent used herein, ethers such as tetrahydrofuran are preferable.

The reaction temperature is generally room temperature to 80° C., and the reaction time is approximately 1 to 24 hours.

The compound produced by the above described method can be isolated and purified according to a known method such as extraction, precipitation, distillation, chromatography, fractional recrystallization, or recrystallization.

Moreover, when the compound or a production intermediate has asymmetric carbon(s), optical isomers are present. These optical isomers can each be isolated and purified by a conventional method such as fractional recrystallization (salt fractionation) involving recrystallization with an appropriate salt, or column chromatography. A reference document for a method of fractionating an optical isomer from a racemate can be Jacques et al., "Enantiomers, Racemates and Resolution, John Wiley And Sons, Inc.".

Crystals of the salt of the compound of the present invention can be obtained by the following method.

(Method for Producing α Crystals)

For example, (1) a free-form compound and a base or acid are dissolved in a solvent to prepare a solution,
(2) then insoluble matter in the solution is filtered,
(3) the temperature of the filtered solution is increased to approximately 40° C. to 50° C., and stirring is continued,
(4) the solution obtained after the stirring is cooled to approximately room temperature to obtain crystals, and
(5) the crystals are collected by filtration, and are then dried under reduced pressure at approximately 40° C., so as to obtain the crystals of interest.

Examples of the base used in (1) above include: alkali metal hydroxides, such as sodium hydroxide, potassium hydroxide, and lithium hydroxide; alkaline-earth metal hydroxides, such as magnesium hydroxide or calcium hydroxide; organic bases such as N-methylmorpholine, triethylamine, tributylamine, diisopropylethylamine, dicyclohexylamine, N-methylpiperidine, pyridine, 4-pyrrolidinopyridine, piperazine, or picoline; and amino acids such as glycine, lysine, arginine, ornithine, glutamic acid, or aspartic acid. Preferred examples of the base include sodium hydroxide, potassium hydroxide, and piperazine.

Examples of the acid used in (1) above include: inorganic acids such as hydrohalic acids including hydrofluoric acid, hydrochloric acid, hydrobromic acid, or hydroiodic acid, nitric acid, perchloric acid, sulfuric acid, or phosphoric acid; and organic acids, such as lower alkanesulfonic acids including methanesulfonic acid, trifluoromethanesulfonic acid, or ethanesulfonic acid, arylsulfonic acids including benzenesulfonic acid or p-toluenesulfonic acid, acetic acid, malic acid, fumaric acid, succinic acid, citric acid, ascorbic acid, tartaric acid, oxalic acid, or maleic acid, and a more preferred example of the acid is p-toluenesulfonic acid.

The solvent used in (1) above is not particularly limited, as long as it is an inert solvent that does not affect the stability of a compound. A preferred example of the solvent is a mixed solvent consisting of alcohols such as methanol, ethanol or propanol, and water.

(Method for Producing β Crystals)

Methanol is added to α-form crystals at room temperature, so that the crystals are completely dissolved therein. Thereafter, acetonitrile is added to the above obtained solution at room temperature to prepare a solution. This solution is left for several days, and thereafter, the precipitated crystals are collected by filtration. Subsequently, the crystals are air-dried to obtain the crystals of interest.

(Method for Producing γ Crystals)

An aqueous sodium hydroxide solution is added to a free-form compound at room temperature, so that the compound is completely dissolved in the aqueous solution. Thereafter, propanol is added to the above obtained solution at room temperature. A vessel containing the obtained solution is hermetically closed, and is then left at rest for approximately 1 month. Thereafter, the precipitated crystals are collected by filtration. Subsequently, the crystals are air-dried to obtain the crystals of interest.

(Method for Producing δ Crystals)

An aqueous sodium hydroxide solution and propanol are added to a free-form compound at room temperature, and the temperature of the mixture is then increased to approximately 40° C., followed by performing stirring for several hours. Thereafter, propanol is further added to the reaction solution, and the obtained mixture is then stirred at approximately 40° C. for several hours. Thereafter, the precipitated crystals are collected by filtration, and are then dried under reduced pressure at 40° C. overnight, so as to obtain the crystals of interest.

(Dosage Form)

Administration may be carried out either by oral administration using a tablet, a pill, a capsule, a granule, a powder, a liquid or the like, or by parenteral administration using an injection such as an intraarticular injection, an intravenous injection or an intramuscular injection, a suppository, an ophthalmic preparation, an eye ointment, a transdermal liquid, an ointment, a transdermal patch, a transmucosal liquid, a transmucosal patch, an inhalant, or the like.

As a solid composition for oral administration, a tablet, a powder, a granule or the like can be used. In such a solid composition, one or two or more active ingredients are mixed with at least one inactive excipient, for example with lactose, mannitol, glucose, hydroxypropyl cellulose, microcrystalline cellulose, starch, polyvinyl pyrrolidone, and/or magnesium aluminometasilicate. The composition may comprise inactive additives, for example a lubricant such as magnesium stearate, a disintegrant such as carboxymethyl starch sodium, a stabilizing agent, and a dissolution aid according to a conventional method. The tablet or pill may be coated with a sugar-coated film, or a film of a gastric or enteric substance, as necessary.

A liquid composition for oral administration comprises a pharmaceutically acceptable emulsion, solution, suspension, syrup, elixir, etc., and it also comprises a commonly used inactive diluent, such as purified water or ethanol. The liquid composition may also comprise an adjuvant such as a solubilizing agent, a wetting agent, or a suspending agent, a sweetening agent, a flavoring agent, a fragrance, and a preservative, as well as an inactive diluent.

An injection for parenteral administration comprises an aseptic aqueous or non-aqueous solution, suspension, or emulsion. Examples of the aqueous solvent include distilled water for injection and normal saline. Examples of the non-aqueous solvent include propylene glycol, polyethylene glycol, vegetable oils such as olive oil, alcohols such as ethanol, and polysorbate 80. Such a composition may further comprise a tonicity agent, a preservative, a wetting agent, an emulsifying agent, a dispersing agent, a stabilizing agent, or a dissolution aid. These are sterilized, for example, by filtration using a bacteria-holding filter, or by blending of a bactericide or irradiation. Moreover, it also possible that an aseptic solid composition is produced, and that the solid composition is dissolved or suspended in sterile water or an aseptic solvent for injection before use, and is then used.

Examples of an external agent include an ointment, a plaster, a cream, a jelly, a cataplasm, a spray, a lotion, an ophthalmic preparation, and an eye ointment. The external agent comprises a commonly used ointment base, lotion base, aqueous or non-aqueous liquid, suspension, emulsion, etc. Examples of such an ointment or lotion base include polyethylene glycol, propylene glycol, white Vaseline, bleached beeswax, polyoxyethylene hydrogenated castor oil, glyceryl monostearate, stearyl alcohol, cetyl alcohol, lauromacrogol, and sorbitan sesquioleate.

As a transmucosal agent such as an inhalant or a transnasal agent, a solid, liquid, or semi-solid type is used, and it can be produced according to a conventionally known method. For example, a known excipient, and further, a pH adjusting agent, a preservative, a surfactant, a lubricant, a stabilizing agent, a thickening agent, etc. may be added, as appropriate. For administration, a device suitable for inhalation or insufflation can be used. For instance, using a known de vice such as a metered-dose inhaler or a sprayer, the compound can be administered alone or in the form of a powder of a formulated mixture, or in the form of a solution or a suspension in combination with a pharmaceutically acceptable carrier. A dry powder inhaler or the like may be used for single administration or multiple administration, and a dry powder or a powder-containing capsule can be used. Alternatively, the transmucosal agent may also have the form of a pressurized aerosol spray or the like, in which a suitable ejector, for example, chlorofluoroalkane, hydrofluoroalkane or a preferred gas such as carbon dioxide is used.

(Dose)

In the case of general oral administration, it is adequate that the dose per day is approximately 0.001-100 mg/kg, preferably 0.1-30 mg/kg, more preferably 0.1-10 mg/kg body weight. The oral agent is administered once or divided over two or more administrations. In the case of intravenous administration, the dose per day is suitably approximately 0.0001-10 mg/kg body weight, and such a dose of compound is administered once a day or divided over several administrations. Moreover, a transmucosal agent is administered at a dose of approximately 0.001-100 mg/kg body weight once a day or divided over several administrations. Taking into consideration symptoms, age, sex, etc., the applied dose is determined, as appropriate, depending on the individual case.

(Combined Use)

The compound of the present invention can be used in combination with various therapeutic agents or preventive agents for diseases, in respect of which the present compound is considered to exhibit effectiveness. In the combined use, the present compound and other agents may be coadministered, or the present compound and the other agents may be administered separately, continuously or with desired intervals. The preparations for coadministration may be either combination drugs, or preparations that are formulated separately.

(Formulation Example 1) Powder 5 g of a salt, or hydrate thereof, of the compound of the present invention, 895 g of lactose and 100 g of corn starch are mixed using a blender to obtain a powder.

(Formulation Example 2) Granules 5 g of a salt, or hydrate thereof, of the compound of the present invention, 865 g of lactose and 100 g of low substituted hydroxypropyl cellulose are mixed, and thereafter 300 g of a 10% aqueous hydroxypropyl cellulose solution is added to the mixture, followed by kneading it. The kneaded product is granulated using an extrusion granulator and is then dried to obtain granules.

(Formulation. Example 3) Tablet 5 g of a salt, or hydrate thereof, of the compound of the present invention, 90 g of lactose, 34 g of corn starch, 20 g of crystalline cellulose, and 1 g of magnesium stearate are mixed using a blender, and the obtained mixture is subjected to a tablet-making machine to obtain a tablet.

The pharmacological activity of crystals of a salt of the compound of the present invention was confirmed by the following test.

(Test Example) Rat $^{33}$P Phosphate Oral Challenge Test (Intestinal Phosphate Absorption Suppression Test)

Using male SD rats (5-7 weeks old) that had been fasted on the previous day, the compound described in the Examples was suspended or dissolved in a solvent such as 0.5% methyl cellulose (3-6 mg/mL), and the thus obtained solution was administered to each rat at a dose of 30 mg/kg by forced oral administration. On the other hand, regarding a control group, the solvent was administered to each rat at a dose of 5 mL/kg. Thirty minutes after administration, a $^{32}$P phosphate solution (8.3 mM NaH$_2$PO$_4$, 0.35 MBq/mL) was administered to the rats at a dose of 7.2 mL/kg by forced oral administration. Then, 15, 30, 60, and 120 minutes after administration, blood was collected from the jugular vein of each rat under anesthesia with isoflurane. The radioactivity in 50 of serum was measured using a liquid scintillation counter, and the AUC$_{0\text{-}60\ min}$ was then calculated from the radioactivity value. The obtained value was defined as an amount of phosphate absorbed. The phosphate absorption-inhibiting activity of the compound was calculated according to the following expression.

Phosphate absorption-inhibiting activity (%)=[(100−the amount of phosphate absorbed in the compound administration group)/the amount of phosphate absorbed in the control group]×100

TABLE 1

| Example No. | Phosphorus absorption-inhibiting activity (%) |
|---|---|
| 1 | 72 |
| 6 | 59 |

EXAMPLES

Hereinafter, the present invention will be described in more detail in the following Examples. However, these examples are not intended to limit the scope of the present invention.

Abbreviations used in the Examples and the like have the following meanings:
μg: microgram
mg: milligram
g: gram
μL: microliter
mL: milliliter
L: liter
MHz: megahertz
μm: micrometer
rpm: revolutions per minute (number of rotations/minute)
JP1: First fluid for disintegration test of Japanese Pharmacopoeia
JP2: Second fluid for disintegration test of Japanese Pharmacopoeia
Mc: diluted McIlvaine buffer
NaOH: sodium hydroxide
KOH: potassium hydroxide
Acetone: acetone
1-PrOH: 1-propanol
THF: tetrahydrofuran
DCM: dichloromethane
DMF: N,N-dimethylformamide
THF: tetrahydrofuran
DIPEA: diisopropylethylamine
WSC: 1-ethyl-3-(3-dimethylaminopropyl)carbodiimide hydrochloride (Water Soluble Carbodiimide)
HBTU: 1-[bis(dimethylamino)methylene]-1H-benzotriazolium-3-oxide hexafluorophosphate
DTA: Differential Thermal Analysis
TG: Thermo Gravimetry
TGA: Thermo Gravimetry Analyzer
RH: Relative Humidity In the following Examples,
the measurement of powder X-ray diffraction was carried out by employing a horizontal sample stage type strong X-ray diffractometer, RINT-TTR III., manufactured by Rigaku Corporation.

The measurement was carried out by employing the horizontal sample stage type strong X-ray diffractometer, RINT-TTR III., manufactured by Rigaku Corporation, under the following measurement conditions.
Radiation source: CuKα-ray
Wavelength: 1.54056 Å
Measured diffraction angle range (2θ): 2° to 40°
Sampling width: 0.02°
Scanning speed: 20°/minute
Tube voltage: 50 kV
Tube current: 300 mA
Divergence slit: 0.5 mm
Scattering slit: 0.5 mm
Receiving slit: 0.5 mm Devices involving data processing were handled according to the methods and procedures instructed in individual devices. It is to be noted that the diffraction angle and the diffraction intensity fluctuate somewhat depending on the direction of crystal growth, particle size, measurement conditions, and the like.

The longitudinal axis of a view showing the powder X-ray diffraction pattern obtained by the present device indicates the diffraction intensity in a unit of count/second (cps), and the horizontal axis thereof indicates the value of the diffraction angle 2θ.

The thermogravimetry-differential thermal analysis (TG-DTA) was carried out by using TG-DTA6200 manufactured by SII Nanotechnology.

Approximately 4 mg of a sample was filled into a special sample pan made of aluminum. The measurement range was set from 20° C. or 30° C. to 380° C., and the temperature-increasing rate was set at 10° C./minute. The change in the amount of heat generated between the sample and a reference (a vacant sample pan made of aluminum) was continuously measured and recorded under a nitrogen atmosphere. It is to be noted that devices involving data processing were handled according to the methods and procedures instructed in individual devices. The longitudinal axis of a TG-DTA curve obtained by the present device indicates a temperature difference (DTA) and a weight change (TG), and the horizontal axis thereof indicates a temperature (° C.). In addition, the solid line indicates a DTA curve, and the dotted line indicates a TG curve.

Hygroscopicity was measured by using a moisture balance system, VTI SGA-CX, manufactured by TA instruments, Japan.

Approximately 10 mg of a sample was filled into a special sample holder, and the relative humidity was then changed by 10% from 10% RH to 90% RH at 25° C., thereby measuring the change in the mass.

Each measurement was carried out under the following conditions, and devices involving data processing were handled according to the methods and procedures instructed in individual devices. The longitudinal axis of an isothermal humidification-dehumidification curve obtained by the present device indicates the change (%) in the weight of a compound, and the horizontal axis indicates the humidity (% RH.).
Drying: OFF (without previous drying)
Temperature: 25° C.
Equilibrium criterion: 0.03 wt % in 15 min
Max equilibrium time: 120 min.
Relative humidity steps:
40, 10, 20, 30, 40, 50, 60, 70, 80, 90, 80, 70, 60, 50, 40, 30, 20, and 10% RH In nuclear magnetic resonance (hereinafter referred to as $^1$H NMR) spectra, the chemical shift value was described at a δ value (ppm), using tetramethylsilane as a standard substance. With regard to splitting patterns, a singlet is represented by s, a doublet is represented by d, a triplet is represented by t, a quartet is represented by q, and a multiplet is represented by m, and broad is represented by br.

With regard to the measurement of solubility, solubility was calculated by the following operations.

Approximately 5 mg of a sample was weighed into a test tube, and then 5 mL each solution (see below) that had previously been set at 37° C. was added to the test tube.

Using Thermomixer Comfort (a shaker) manufactured by Eppendorf, the test tube was intensively shaken at 37° C. for 30 seconds at 750 rpm, and was then left at rest for 4 minutes 30 seconds. This shaking and resting operation was repeated 5 times (30 minutes in total).

Thereafter, the test tube was continuously shaken at 37° C. for 23.5 hours (750 rpm). The solutions obtained 30 minutes and 24 hours after initiation of the shaking were promptly filtered through a membrane filter (pore diameter: 0.45 μm), and the obtained filtrates were each diluted with a sample solution to an appropriate concentration. The concentration of a compound in the filtrate was measured by UHPLC, and solubility was then calculated.

The following solutions were used.
JP1: 2.0 g of sodium chloride was dissolved in 7.0 mL of hydrochloric acid and water to prepare 1000 mL of a solution (pH: about 1.2).
JP2: 118 mL of a 0.2 mol/L sodium hydroxide test solution and water were added to 250 mL of a 0.2 mol/L potassium dihydrogen phosphate test solution to prepare 1000 mL of a solution (pH: about 6.8).
Water: Ultrapure water (for use in LC/MS) manufactured by Wako Pure Chemical Industries, Ltd. was used.
Mc pH 6.0: A diluted McIlvaine buffer (pH 6.0) manufactured by Kanto Chemical Co., Inc. was used.
Mc pH 7.5: A diluted McIlvaine buffer (pH 7.5) manufactured by Kanto Chemical Co., Inc. was used.

Conditions for HPLC are as follows.
Apparatus: UHPLC H-Class manufactured by Waters
Mobile phase: A: 0.01 mol/L aqueous potassium phosphate solution (pH 4.0); B: acetonitrile
Flow rate: 0.5 mL/minute
Column: Acquity UPLC BEH C18, 2.1 mm ID×75 mm, particle diameter: 1.7 μm (Waters)
Column temperature: 40° C.
Gradient conditions: Concentration of liquid B: 5% to 80% (0 to 10 minutes), 80% (10 to 12 minutes), 80% to 5% (12 to 12.01 minutes), and 5% (12.01 to 15 minutes)
Poured amount: 3 μL
Detection wavelength: 220 nm Example 1

α Crystals of Disodium 4-[2-(4-{[2-({3-[(trans-4-carboxycyclohexyl) (ethyl) sulfamoyl] benzoyl}amino)-5-(piperidin-1-yl)benzoyl] amino}phenyl)ethyl]benzoate trihydrate Crystals of disodium salt trihydrate (α crystals) of:

[Formula 7]

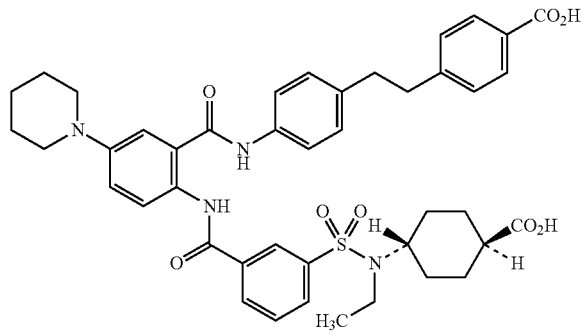

(1)
A 1 mol/L NaOH aqueous solution (3.1 mL) was added to 4-[2-(4-{[2-({3-[(trans-4-carboxycyclohexyl) (ethyl)sulfamoyl]benzoyl}amino)-5-(piperidin-1-yl)benzoyl] amino}phenyl)ethyl]benzoic acid (1.2 g), and the compound was then completely dissolved in the aqueous solution. Thereafter, acetonitrile (60 ml) was added to the obtained solution, and the mixed solution was stirred at room temperature for 1 day, and thereafter, it was further stirred at 40° C. for 1 day. The precipitated solid was collected by filtration, and was then dried under reduced pressure at room temperature for 3 hours to obtain 1.1 g of the title compound (85%).

(2)
Water (46.4 mL), 1-PrOH (72 mL), and a 4 mol/L NaOH aqueous solution (25.54 ml) were added to 4-[2-(4-{[2-({3-[(trans-4-carboxycyclohexyl) (ethyl) sulfamoyl] benzoyl}amino)-5-(piperidin-1-yl)benzoyl]amino}phenyl) ethyl]benzoic acid (40.0 g). The mixed solution was stirred at room temperature, and thereafter, insoluble matter was filtered, followed by washing with water/1-PrOH (3:7, 80 ml). The temperature of the filtrate was increased to 40° C., 1-PrOH (160 ml) was then added to the filtrate, and a seed crystal (α crystal, 0.2 g) was further added thereto. Thereafter, the temperature of the mixture was increased to 50° C., 1-PrOH (96 ml) was added thereto, and the thus obtained mixture was then stirred overnight. Thereafter, 1-PrOH (480 ml) was added to the reaction solution, and the obtained mixture was then stirred overnight. Subsequently, the reaction solution was then cooled to room temperature, and the precipitated solid was then collected by filtration. Thereafter, the solid was dried under reduced pressure at 40° C. overnight to obtain 39.4 g of the title compound (96%).

(3)
Water (25.5 mL), acetone (7.5 mL), and a 25% NaOH aqueous solution (4.2 g) were added to 4-[2-(4-{[({3-[(trans-4-carboxycyclohexyl)(ethyl)sulfamoyl]benzoyl}amino)-5-(piperidin-1-yl)benzoyl]amino}phenyl)ethyl]benzoic acid (10.0 g). The mixed solution was stirred at room temperature, and thereafter, insoluble matter was filtered, followed by washing with water/acetone (3:5, 12 ml). The temperature of the filtrate was increased to 40° C. acetone (48.0 ml) was then added to the filtrate, and a seed crystal (α crystal, 0.05 g) was further added thereto. Thereafter, acetone (39.0 ml) was added to the mixture, and a mixture of α crystals and ε crystals precipitated from a supersaturated state was then stirred overnight. Subsequently, a small amount of crystals was collected, and it was confirmed by powder X-ray diffractometry that only α crystals were present. After that, acetone (90.0 ml) was added thereto, the mixture was then cooled to room temperature, and it was then stirred overnight. Thereafter, the precipitated solid was collected by filtration, and was then dried under reduced pressure at 40° C. overnight to obtain 9.7 g of the title compound (88%).

A powder X-ray diffraction pattern of the mixture of α crystals and ε crystals is shown in FIG. 1.

Characteristic peaks (2θ(°)) of the ε crystals in the powder X-ray (radiation source Cu): around 5.97, around 8.48, around 8.97, around 9.55, and around 11.22.

Figure 2:
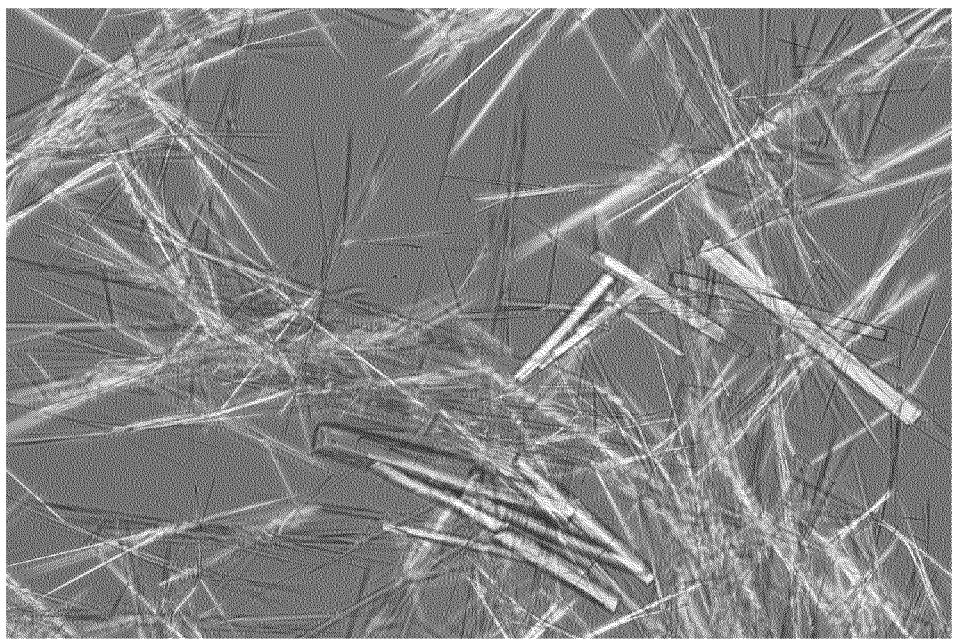
FIG. 2 is a view showing the polarizing microscopic photograph of Example 1 (a mixture of α crystals and ε crystals).

A polarizing microscopic photograph of the mixture of α crystals and ε crystals is shown in FIG. 2.

Figure 3:
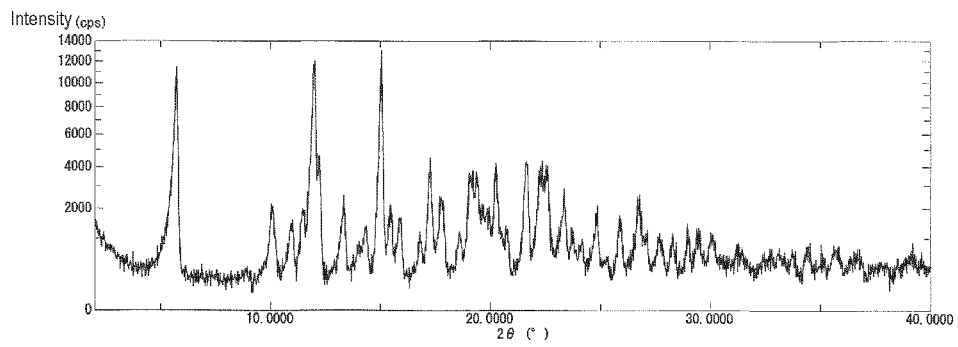
FIG. 3 is a view showing the powder X-ray diffraction pattern of Example 1 (α crystals).

A powder X-ray diffraction pattern of the α crystals is shown in FIG. 3.

Characteristic peaks (2θ(°)) of the α crystals in the powder X-ray (radiation source Cu): around 5.72, around 10.10, around 10.96, around 11.98, around 13.34, around 15.02, around 17.26, around 20.26, around 21.66, and around 22.36.

Figure 11:
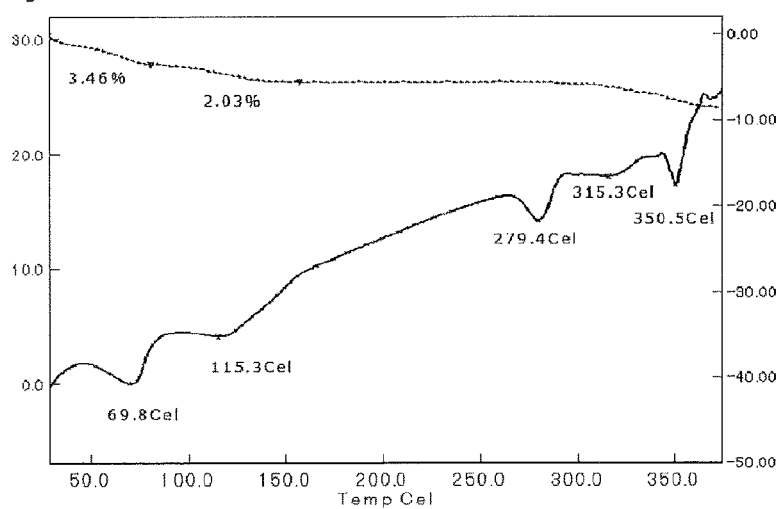
FIG. 11 is a view showing the results of the thermogravimetry-differential thermal analysis (TG-DTA) of Example 1.

The results of a thermogravimetry-differential thermal analysis (TG-DTA) are shown in FIG. 11.

Figure 19:
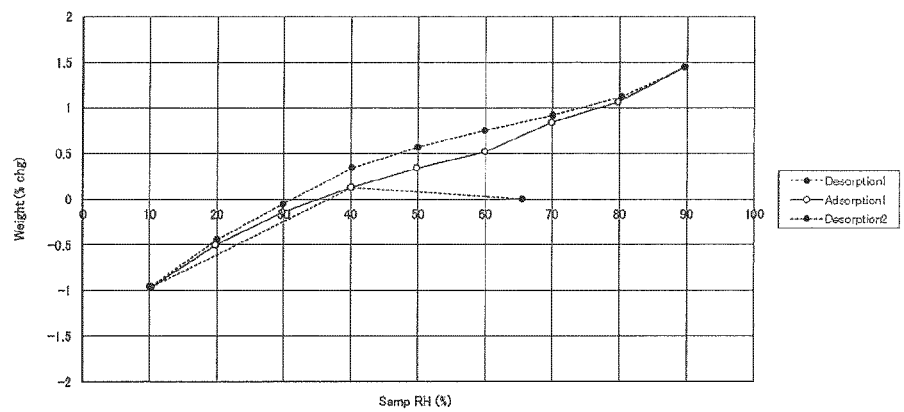
FIG. 19 is a view showing the measurement results of hygroscopicity of Example 1.

The measurement results of hygroscopicity are shown in FIG. 19.

$^1$H NMR spectrum (400 MHz, CD$_3$OD):
δ: 8.40 (1H, t, J=1.6 Hz), 8.33 (1H, d, J=9.0 Hz), 8.15 (1H, dt, J=7.8, 1.4 Hz), 8.05 (1H, dt, J=8.0, 1.4 Hz), 7.84

(2H, d, J=8.6 Hz), 7.73 (1H, t, J=8.0 Hz), 7.56 (2H, d, J=8.6 Hz), 7.42 (1H, d, J=2.7 Hz), 7.22-7.16 (5H, m), 3.69-3.60 (1H, m), 3.26-3.23 (6H, m), 2.93 (4H, s), 2.01-1.86 (3H, m), 1.79-1.73 (4H, m), 1.65-1.56 (4H, m), 1.52-1.36 (4H, m), 1.22 (3H, t, J=6.5 Hz)

Elemental analysis (measurement values): C: 58.42, H: 6.05, N: 6.38, S: 3.66, and Na: 5.32

Measurement of Solubility:

Under shaking conditions at 37° C. for 30 minutes:

JP1: 1.0 µg/mL, JP2: 40.3 µg/mL, water: 949.4 µg/mL, Mc pH 6.0: 1.1 µg/mL

Under snaking conditions at 37° C. for 24 hours:

JP1: 1.3 JP2: 10.7 water: 960.1 µg/mL, diluted McIlvaine buffer pH 6.0: 0.1 µg/mL Example 2

β Crystals of Disodium 4-[2-(4-{[2-({3-[(trans-4-carboxycyclohexyl) (ethyl)sulfamoyl] benzoyl}amino)-5-(piperidin-1-yl)benzoyl] amino}phenyl)ethyl]benzoate hydrate Crystals of disodium salt hydrate (β crystals) of:

[Formula 8]

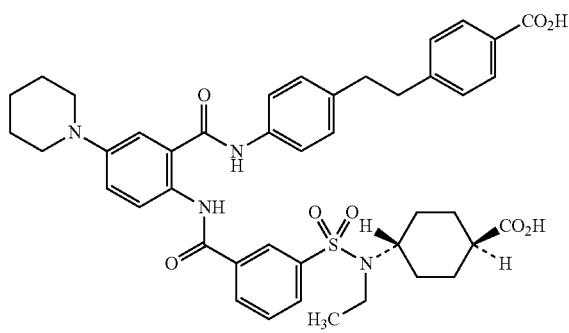

Methanol (66 mL) was added to the α crystals (0.2 g) of disodium 4-[2-(4-{[2-({3-[(trans-4-carboxycyclohexyl)(ethyl)sulfamoyl]benzoyl}amino)-5-(piperidin-1-yl)benzoyl]amino}phenyl)ethyl]benzoate hydrate at room temperature, and the crystals were completely dissolved in the methanol. Then, acetonitrile (80 mL) was added to this solution (16 mL) at room temperature. The thus completely dissolved liquid was left for 4 days, and the precipitated crystals were then collected by filtration. Thereafter, the crystals were air-dried to obtain 22 mg of the title compound (46%).

Figure 4:
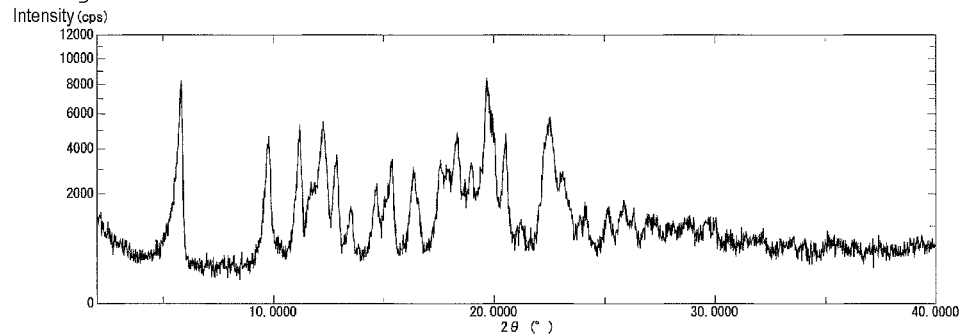
FIG. 4 is a view showing the powder X-ray diffraction pattern of Example 2.

A powder X-ray diffraction pattern is shown in FIG. 4.

Characteristic peaks (2θ(°)) in the powder X-ray (radiation source Cu): around 5.82, around 9.78, around 11.18, around 12.26, around 12.86, around 15.38, around 16.34, around 18.34, around 19.68, and around 22.54.

Figure 12:
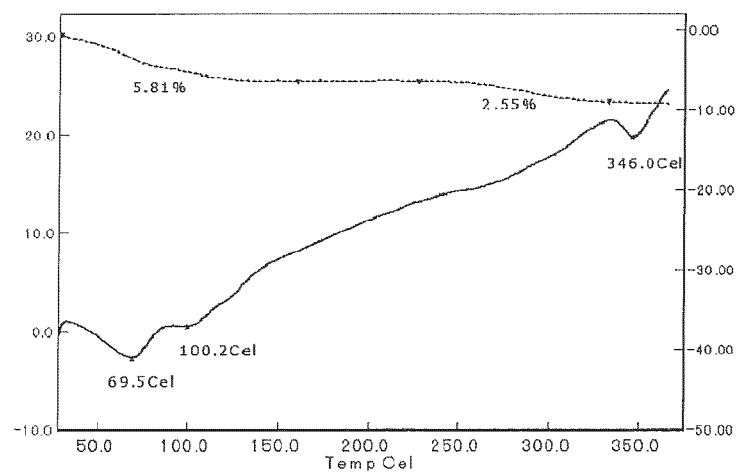
FIG. 12 is a view showing the results of the thermogravimetry-differential thermal analysis (TG-DTA) of Example 2.

The results of a thermogravimetry-differential thermal analysis (TG-DTA) are shown in FIG. 12.

Example 3

γ Crystals of Disodium 4-[2-(4-{[2-({3-[(trans-4-carboxycyclohexyl)(ethyl)sulfamoyl] benzoyl}amino)-5-(piperidin-1-yl)benzoyl] amino}phenyl)ethyl]benzoate hydrate Crystals of disodium salt hydrate (γ crystals) of:

[Formula 9]

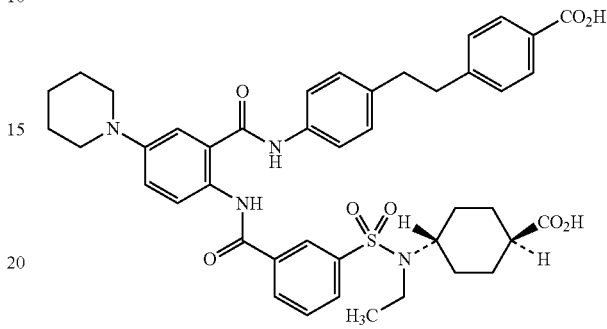

A 1 mol/L NaOH aqueous solution (1345 µL) was added to 4-[2-(4-{[2-({3-[(trans-4-carboxycyclohexyl)(ethyl)sulfamoyl]benzoyl}amino)-5-(piperidin-1-yl)benzoyl]amino}phenyl)ethyl]benzoic acid (0.5 g) at room temperature, and the compound was completely dissolved in the aqueous solution. Then, 1-PrOH (200 µL) was added to this solution (100 µL) at room temperature. The vessel was hermetically closed, and it was then left at rest for approximately 1 month. Thereafter, the precipitated crystals were collected by filtration, and were then air-dried to obtain 12 mg of the title compound (31%).

Figure 5:
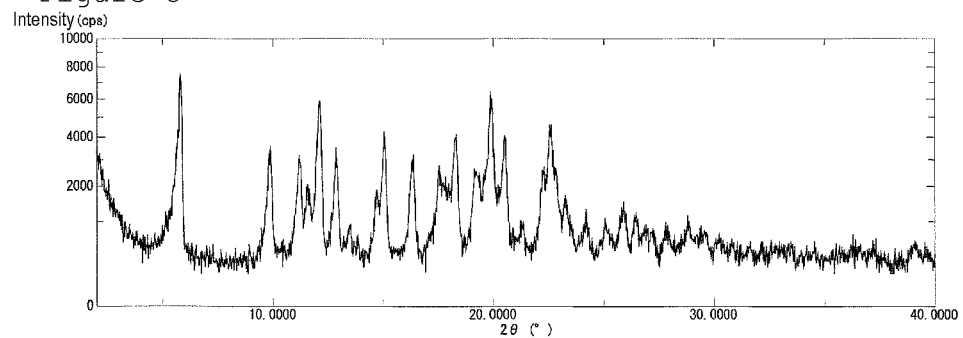
FIG. 5 is a view showing the powder X-ray diffraction pattern of Example 3.

A powder X-ray diffraction pattern is shown in FIG. 5.

Characteristic peaks (2θ(°)) in the powder X-ray (radiation source Cu): around 5.80, around 9.86, around 12.12, around 12.86, around 15.04, around 16.30, around 18.28, around 19.90, around 20.52, and around 22.58.

Figure 13:
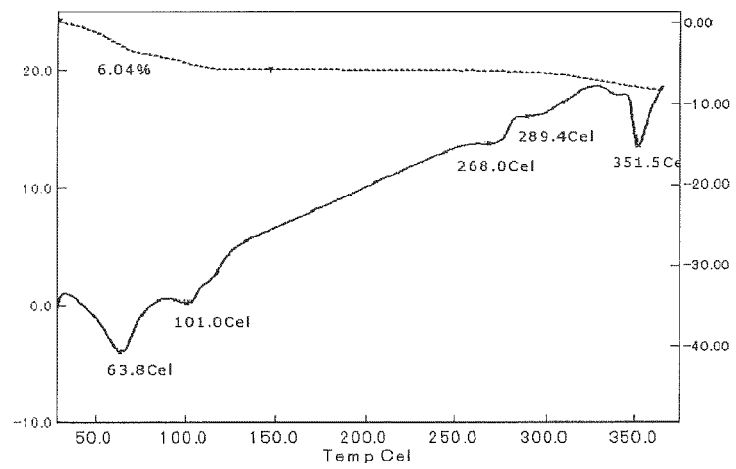
FIG. 13 is a view showing the results of the thermogravimetry-differential thermal analysis (TG-DTA) of Example 3.

The results of a thermogravimetry-differential thermal analysis (TG-DTA) are shown in FIG. 13.

Example 4

δ Crystals of disodium 4-[2-(4-{[2-({3-[(trans-4-carboxycyclohexyl)(ethyl)sulfamoyl] benzoyl}amino)-5-(piperidin-1-yl)benzoyl] amino}phenyl)ethyl]benzoate hydrate Crystals of disodium salt hydrate (δ crystals) of:

[Formula 10]

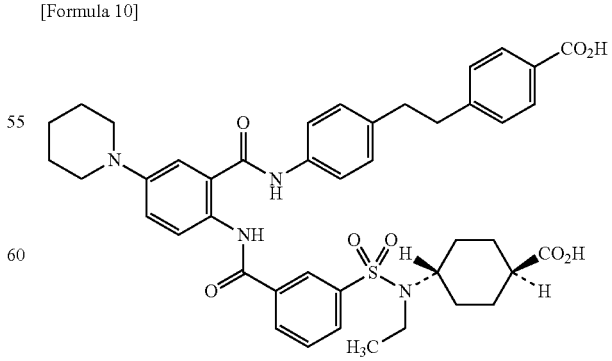

A 4 mol/L NaOH aqueous solution (640 µL), water (1.76 mL), and 1-EtOH (3.2 mL) were added to 4-[2-(4-{[2-({3-

[(trans-4-carboxycyclohexyl)(ethyl)sulfamoyl]benzoyl}amino)-5-(piperidin-1-yl)benzoyl]amino}phenyl)ethyl]benzoic acid (1.0 g) at room temperature. The temperature of the mixed solution was increased to 40° C., the mixed solution was then stirred for approximately 4 hours, and 1-PrOH (18.4 mL) was then added to the reaction solution. The obtained mixture was stirred at 40° C. for approximately 2 hours, and the precipitated solid was then collected by filtration. Thereafter, the crystals were dried under seduced pressure at 40° C. overnight to obtain 0.9 g of the title compound (83%).

Figure 6:
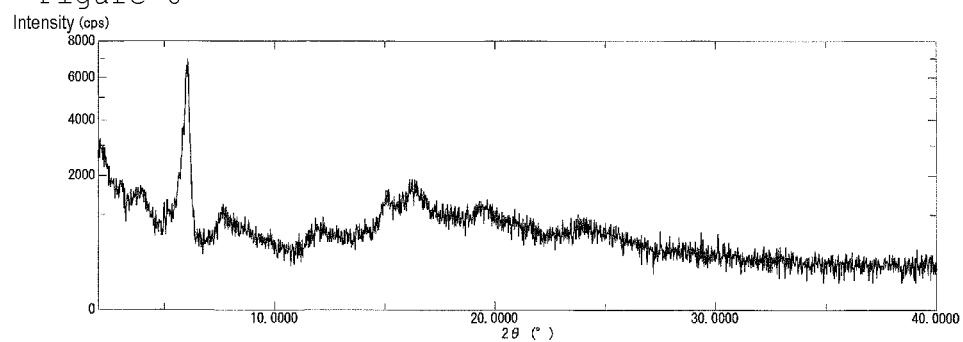
FIG. 6 is a view showing the powder X-ray diffraction pattern of Example 4.

A powder X-ray diffraction pattern is shown in FIG. 6.

A characteristic peak (2θ(°)) was found only at around 6.04 in the powder. X-ray (radiation source Cu).

Figure 14:
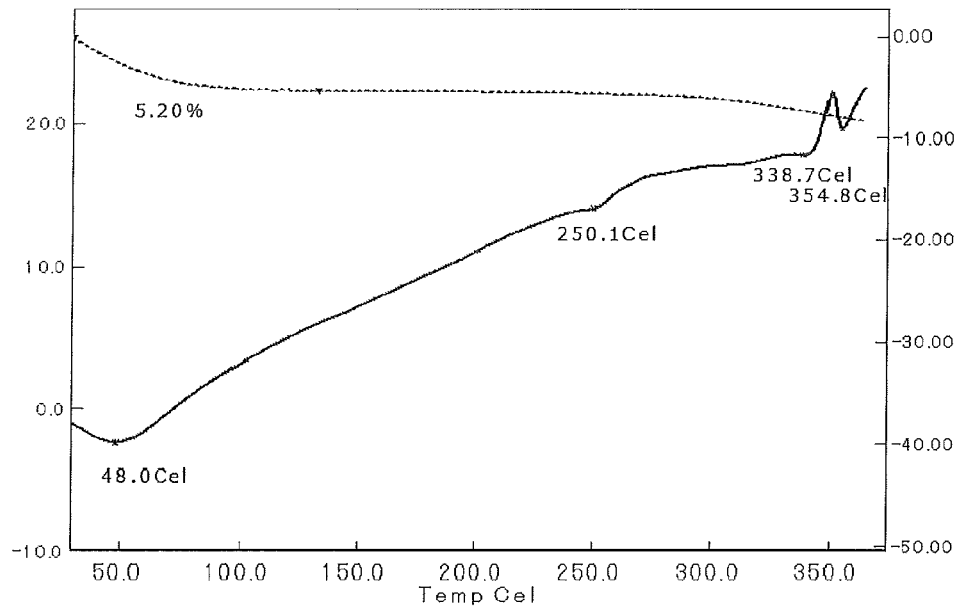
FIG. 14 is a view showing the results of the thermogravimetry-differential thermal analysis (TG-DTA) of Example 4.

The results of a thermogravimetry-differential thermal analysis (TG-DTA) are shown in FIG. 14.

Example 5

Crystals of dipotassium 4-[2-(4-{[2-({3-[(trans-4-carboxycyclohexyl)(ethyl)sulfamoyl]benzoyl}amino)-5-(piperidin-1-yl)benzoyl]amino}phenyl)ethyl]benzoate hydrate Crystals of dipotassium salt hydrate of:

[Formula 11]

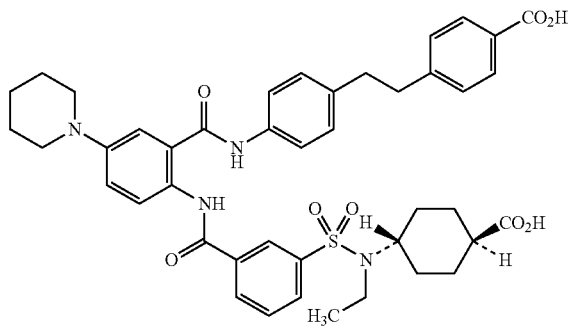

THF (200 mL) was added to 4-[2-(4-{[2-({3-[(trans-4-carboxycyclohexyl)(ethyl)sulfamoyl]benzoyl}amino)-5-(piperidin-1-yl)benzoyl]amino}phenyl)ethyl]benzoic acid (16.4 g), and potassium t-butoxide (4.7 g) was then added thereto at room temperature. Thereafter, methanol (100 mL) was added to the obtained reaction mixture (a majority of the reaction mixture was dissolved in the methanol, but some insoluble matter remained). In order to remove the insoluble matter, the reaction mixture was filtered and was then concentrated. The residue was ground in ethyl acetate, was then filtered, and was then dried under reduced pressure to obtain 16.8 g of a yellow solid (94%). Thereafter, isopropyl acetate/methanol (10:1, 5.5 mL) was added to this solid (250 mg), and the suspension was then stirred at room temperature for 7 days. The obtained solid was filtered and washed with isopropyl acetate, and was then dried under reduced pressure to obtain 241 mg of the title compound (89%).

Figure 7:
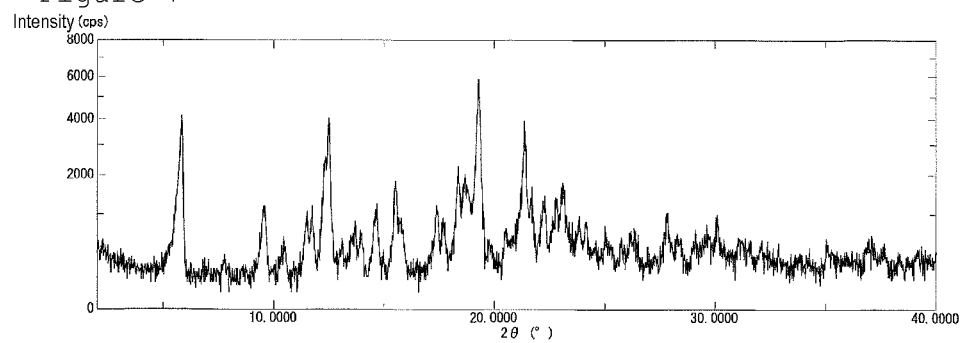
FIG. 7 is a view showing the powder X-ray diffraction pattern of Example 5.

A powder X-ray diffraction pattern is shown in FIG. 7.

Characteristic peaks (2θ(°)) in the powder X-ray (radiation source Cu): around 5.80, around 9.56, around 12.48, around 14.62, around 15.52, around 17.38, around 18.34, around 19.28, around 21.38, and around 23.10.

Figure 15:
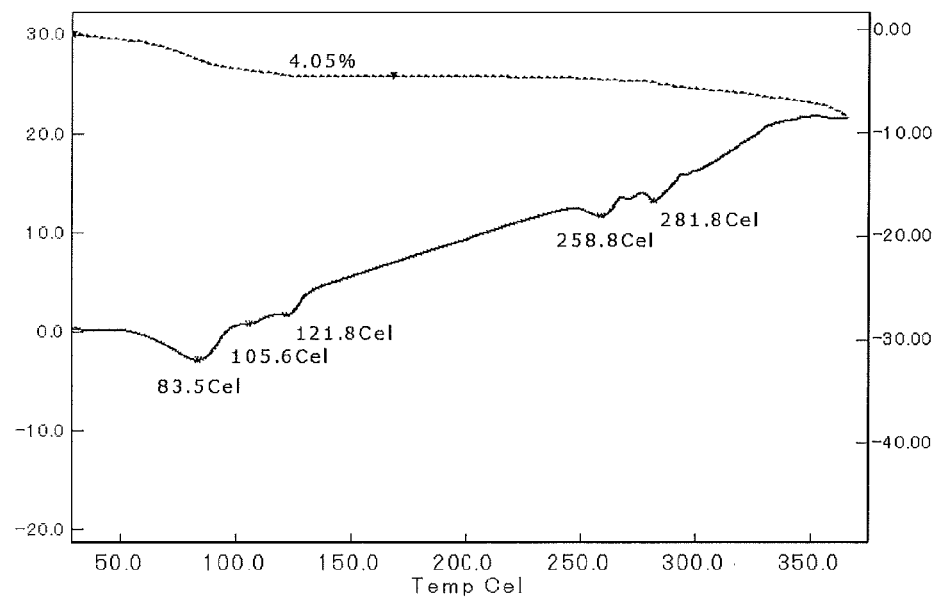
FIG. 15 is a view showing the results of the thermogravimetry-differential thermal analysis (TG-DTA) of Example 5.

The results of a thermogravimetry-differential thermal analysis (TG-DTA) are shown in FIG. 15.

Figure 20:
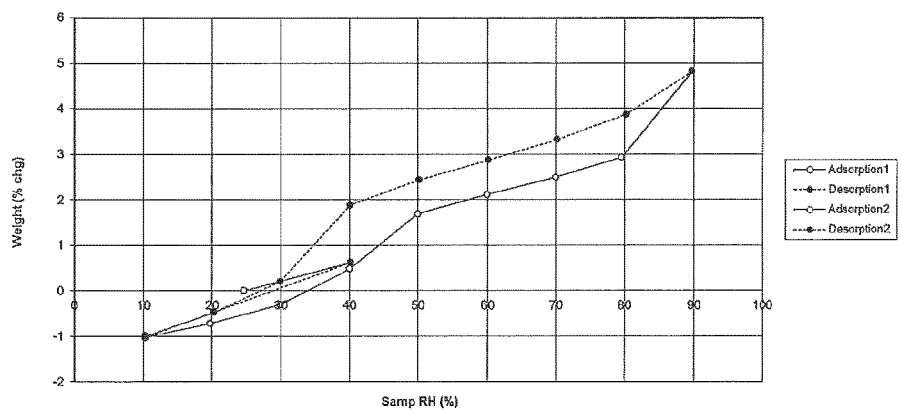
FIG. 20 is a view showing the measurement results of hygroscopicity of Example 5.

The measurement results of hygroscopicity are shown in FIG. 20.

¹H NMR spectrum (400 MHz, CD₃OD):

δ: 8.42 (1H, t, J=1.8 Hz), 8.35 (1H, d, J=9.0 Hz), 8.18 (1H, d, J=7.8 Hz), 8.04 (1H, dt, J=7.8, 1.0 Hz), 7.84 (2H, d, J=7.8 Hz), 7.72 (1H, t, J=7.8 Hz), 7.55 (2H, d, J=8.2 Hz), 7.44 (1H, d, J=2.7 Hz), 7.19-7.14 (5H, m), 3.92 (2H, d, J=6.7 Hz), 3.69-3.62 (1H, m), 3.33-3.27 (2H, m), 2.92 (4H, br s), 1.98-1.87 (3H, m), 1.62-1.35 (6H, m), 1.32-1.27 (1H, m), 1.24 (3H, t, J=6.3 Hz), 0.66-0.61 (2H, m), 0.40-0.36 (2H, m)

Elemental analysis (measurement values): C: 55.84, H: 5.63; N: 6.06; S: 3.38; and K: 8.32

Example 6

Crystals of potassium sodium 4-[2-(4-{[2-({3-[(trans-4-carboxycyclohexyl)(ethyl)sulfamoyl]benzoyl}amino)-5-(piperidin-1-yl)benzoyl]amino}phenyl)ethyl]benzoate hydrate Crystals of monopotassium monosodium salt hydrate of:

[Formula 12]

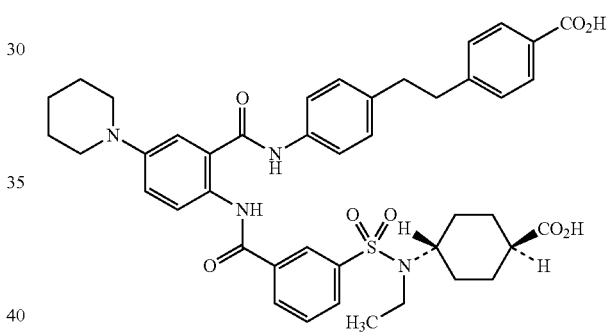

1,4-Dioxane/water/dimethyl sulfoxide (3:1:1, 80 mL) was added to 4-[2-(4-{[2-({3-[(trans-4-carboxycyclohexyl)(ethyl)sulfamoyl]benzoyl}amino)-5-(piperidin-1-yl)benzoyl]amino}phenyl)ethyl]benzoic acid (800 mg), and the compound was completely dissolved in the solution. The mixed solution was freeze-dried with a freeze dryer (Advantage Plus) manufactured by VirTis. Thereafter, a 1 mol/L NaOH aqueous solution (256 was added to the obtained amorphous substance (200 mg) at room temperature, and the substance was completely dissolved in the aqueous solution. Moreover, a 1 mol/KOH aqueous solution (256 μL) was added to the obtained solution at room temperature, and 10 ml of acetone was then added thereto. The obtained mixture was continuously stirred at room temperature for 2 days. Thereafter, the resultant was collected by filtration, and was then dried under reduced pressure to obtain 161 mg of the title compound (75%).

Figure 8:
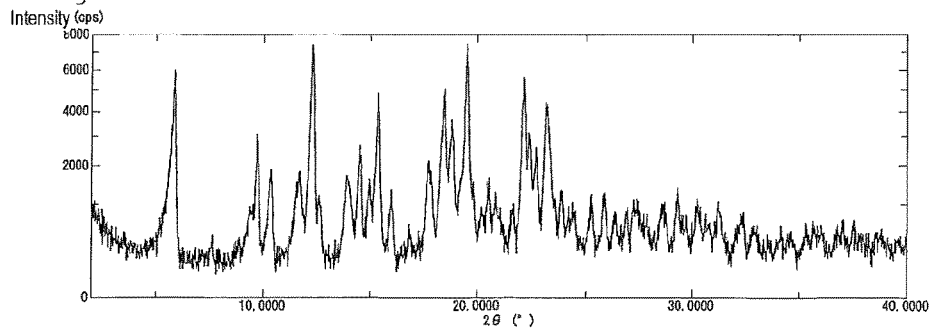
FIG. 8 is a view showing the powder X-ray diffraction pattern of Example 6.

A powder X-ray diffraction pattern is shown in FIG. 8.

Characteristic peaks (2θ(°)) in the powder X-ray (radiation source Cu): around 5.86, around 9.72, around 12.32, around 14.52, around 15.34, around 17.70, around 18.44, around 19.52, around 22.12, and around 23.16.

Figure 16:
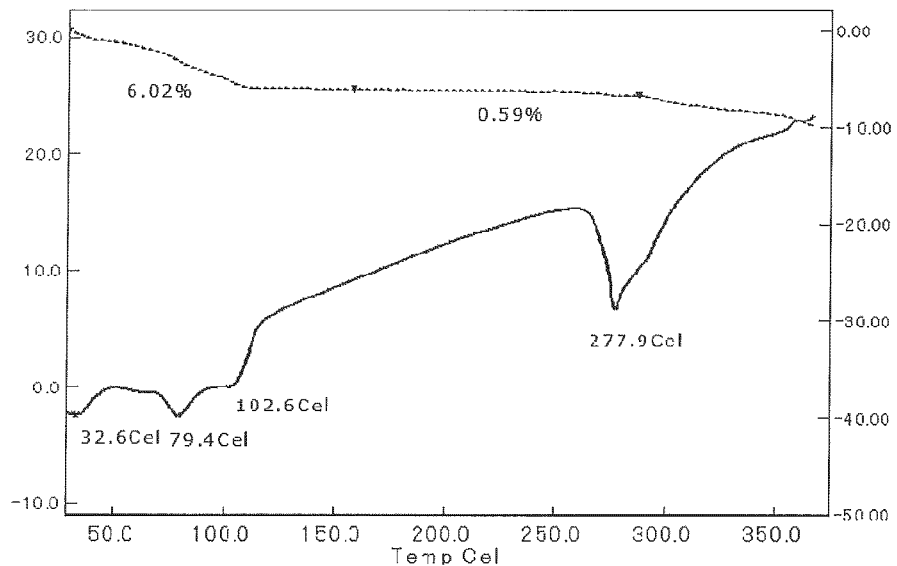
FIG. 16 is a view showing the results of the thermogravimetry-differential thermal analysis (TG-DTA) of Example 6.

The results of a thermogravimetry-differential thermal analysis (TG-DTA) are shown in FIG. 16.

Figure 21:
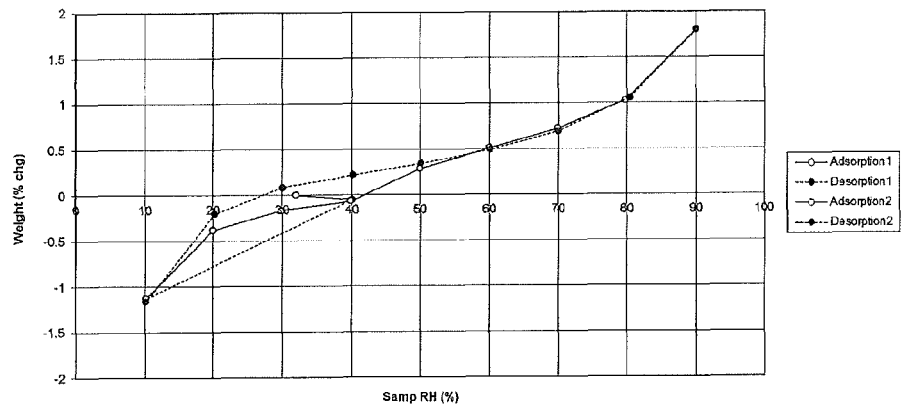
FIG. 21 is a view showing the measurement results of hygroscopicity of Example 6.

The measurement results of hygroscopicity are shown in FIG. 21.

$^1$H NMR spectrum (500 MHz, DMSO-D$_6$+D$_2$O added):

δ: 8.29 (1H, s), 8.15-8.10 (2H, m), 7.98 (1H, =6.2 Hz), 7.74 (3H, t, J=4.0 Hz), 7.57 (2H, d, J=7.1 Hz), 7.37 (1H, s), 7.15 (3H, d, j=7.9 Hz), 7.08 (2H, d, J=8.2 Hz), 3.55-3.49 (1H, m), 24-3.15 (6H, m), 2.85 (4H, s), 1.78 (2H, d, J=11.6 Hz), 1.73-1.62 (5H, m), 1.57-1.53 (21-1, m), 1.42-1.31 (4H, m), 1.21 (2H, ddd, J=24.7, 12.5, 3.8 Hz), 1.13 (3H, t, J=6.9 Hz).

Elemental analysis (measurement values): C: 56.87, H: 5.97, N: 6.08, S: 3.38, Na: 2.78, and K: 4.14.

Measurement of Solubility:

Under shaking conditions at 37° C. for 30 minutes:

JP2: 22.5 μg/mL, water: 2.2 μg/mL

Under shaking conditions at 37° C. for 24 hours:

JP2: 968.5 μg/mL, water: 940.7 μg/mL

Example 7

Crystals of mono-p-toluenesulfonate of 4-[2-(4-{[2-({3-[(trans-4-carboxycyclohexyl)(ethyl)sulfamoyl]benzoyl}amino)-5-(piperidin-1-yl)benzoyl]amino}phenyl)ethyl]benzoic acid Crystals of 1(p-toluenesulfonic acid) salt of:

[Formula 13]

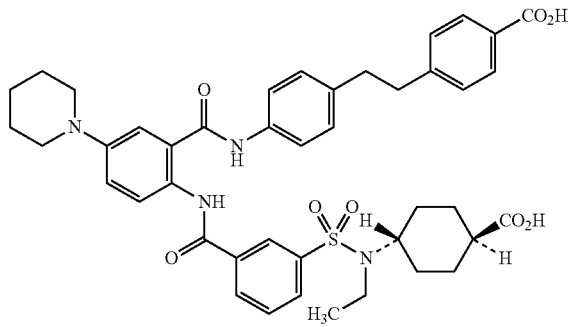

100 mL of acetone was added to 4-[2-(4-{[2-({3-[(trans-4-carboxycyclohexyl) (ethyl)sulfamoyl]benzoyl}amino)-5-(piperidin-1-yl)benzoyl]amino}phenyl)ethyl]benzoic acid (2 g), and thereafter, a 1 mol/L aqueous p-toluenesulfonic acid solution (2.7 mL) was added to the solution at room temperature. The mixed solution was continuously stirred at Loom temperature for 1 day, and the resultant was then collected by filtration. Thereafter, the resultant was dried under reduced pressure to obtain 2.0 g of the title compound (805).

Figure 9:
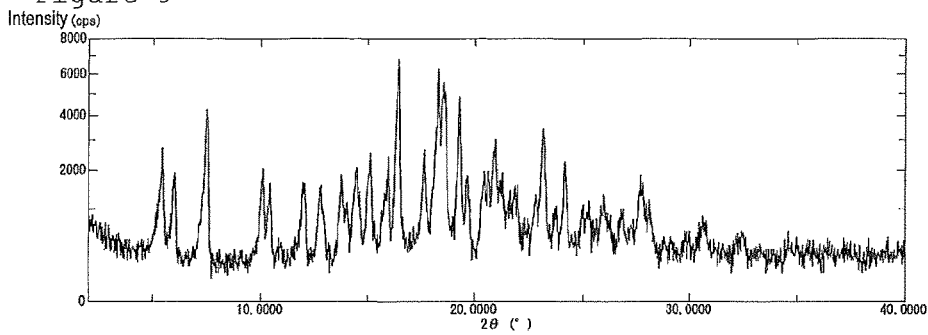
FIG. 9 is a view showing the powder X-ray diffraction pattern of Example 7.

A powder X-ray diffraction pattern is shown in FIG. 9.

Characteristic peaks (2θ(°)) in the powder X-ray (radiation source Cu): around 5.44, around 7.52, around 10.06, around 12.04, around 12.82, around 15.12, around 16.42, around 18.28, around 19.28, and around 23.12.

Figure 17:
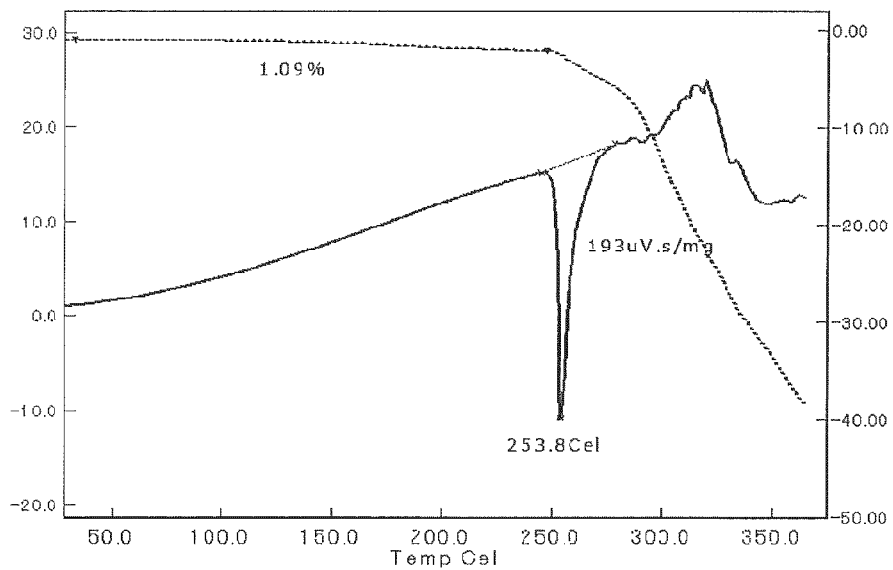
FIG. 17 is a view showing the results of the thermogravimetry-differential thermal analysis (TG-DTA) of Example 7.

The results of a thermogravimetry-differential thermal analysis (TG-DTA) are shown in FIG. 17.

Figure 22:
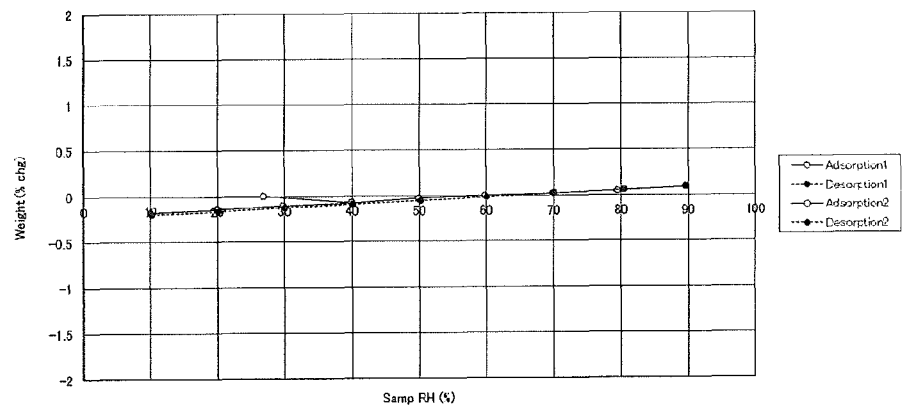
FIG. 22 is a view showing the measurement results of hygroscopicity of Example 7.

The measurement results of hygroscopicity are shown in FIG. 22.

$^1$H NMR spectrum (500 MHz, DMSO-D$_6$):

δ: 11.49 (1H, br s), 10.48 (1H, br s), 8.1-8.24 (2H, m), 8.13 (1H, d, J=6.2 Hz), 8.06 (1H, d, J=8.5 Hz), 7.90-7.45 (2H, br s), 7.84 (2H, d, J=8.2 Hz), 7.78 (1H, t, J=7.8 Hz), 7.58 (2H, d, j=8.5 Hz), 7.47 (2H, dt, J=8.1, 1.8 Hz), 7.33 (2H, d, J=8.5 Hz), 7.19 (2H, d, J=8.5 Hz), 7.11 (2H, dd, J=8.5, 0.6 Hz), 3.64-3.57 (1H, m), 3.47 (4H, br s), 3.22 (23 q, J=7.0 Hz), 2.97-2.87 (4H, m), 2.28 (3H, s), 2.09 (1H, tt, J=12.2, 3.4 Hz), 1.87-1.78 (6H, m), 1.68-1.59 (2H, m), 1.50-1.42 (4H, m), 1.32 (2H, ddd, J=24.8, 12.5, 4.1 Hz), 1.14 (3H, t, J=7.1 Hz)

Elemental analysis (measurement values): C: 62.10, H: 5.95, N: 5.78, and O: 18.55

Measurement of Solubility:

Under shaking conditions at 37° C. for 30 minutes:

JP1: 0.7 μg/mL, JP2: 61.7 μg/mL, water: 0.2 μg/mL, Mc pH 7.5: 639.3 μg/mL

Under shaking conditions at 37° C. for 24 hours:

JP1: 0.1 μL, JP2: 87.5 μg/mL, water: 0.2 μg/mL, diluted McIlvaine buffer pH 6.0: 1058.4 μg/mL Example 8

Crystals of monopiperazine salt of 4-[2-(4-{[2-({3-[(trans-4-carboxycyclohexyl)(ethyl)sulfamoyl]benzoyl}amino)-5-(piperidin-1-yl)benzoyl]amino}phenyl)ethyl]benzoic acid Crystals of monopiperazine salt of:

[Formula 14]

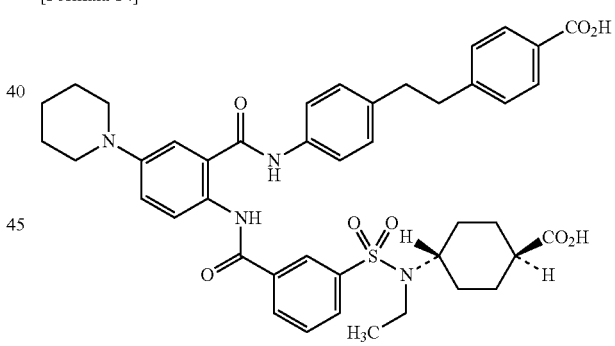

176 mg of anhydrous piperazine and 50 of acetonitrile were added to 4-[2-(4-{[2-({3-[(trans-4-carboxycyclohexyl)(ethyl)sulfamoyl]benzoyl}amino)-5-(piperidin-1-yl)benzoyl]amino}phenyl)ethyl]benzoic acid (800 mg). The mixed solution was continuously stirred at room temperature for 2 days, and the resultant was then collected by filtration. Thereafter, the resultant was dried under reduced pressure to obtain 760 mg of the title compound (85%).

Figure 10:
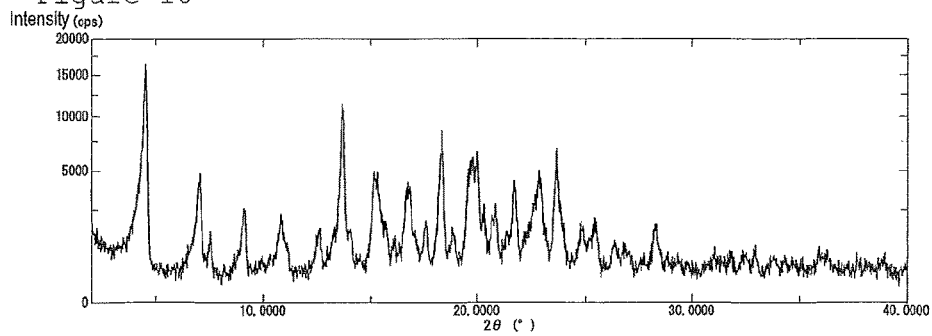
FIG. 10 is a view showing the powder X-ray diffraction pattern of Example 8.

A powder X-ray diffraction pattern is shown in FIG. 10.

Characteristic peaks (2θ(°)) in the powder X-ray (radiation source Cu): around 4.54, around 7.02, around 9.12, around 10.82, around 13.70, around 15.18, around 18.32, around 20.00, around 22.84, and around 23.66.

Figure 18:
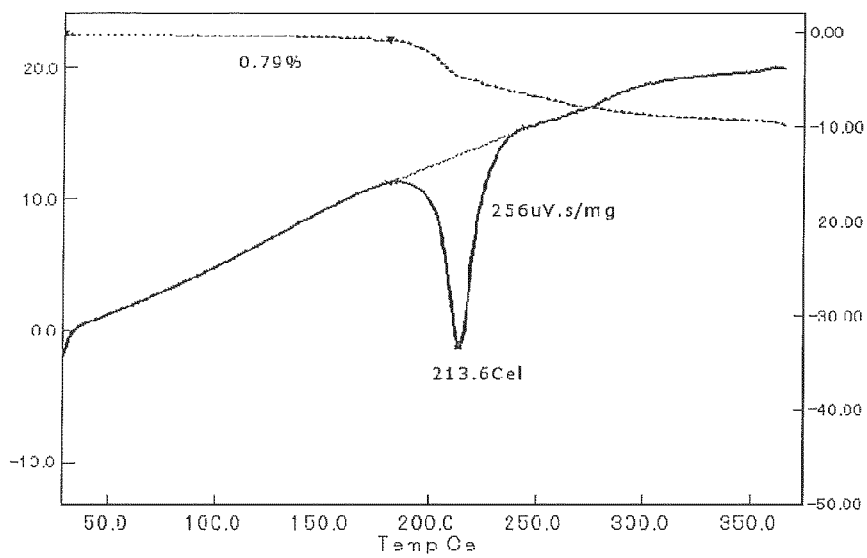
FIG. 18 is a view showing the results of the thermogravimetry-differential thermal analysis (TG-DTA) of Example 8.

The results of a thermogravimetry-differential thermal analysis (TG-DTA) are shown in FIG. 18.

Figure 23:
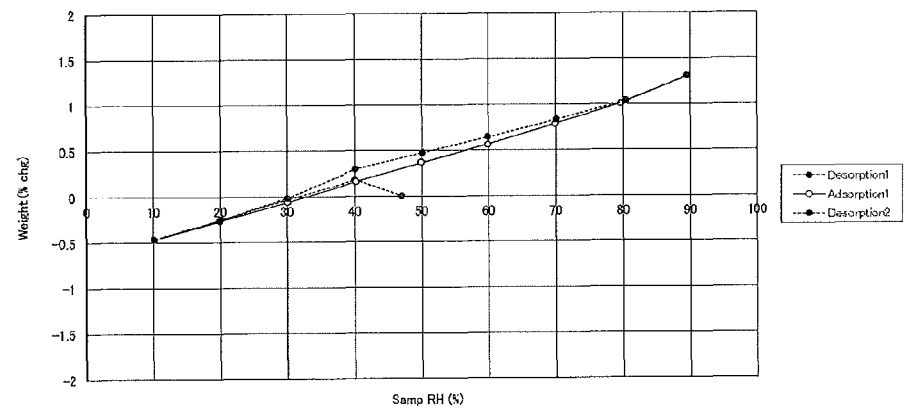
FIG. 23 is a view showing the measurement results of hygroscopicity of Example 8.

The measurement results of hygroscopicity are shown in FIG. 23.

$^1$H NMR spectrum (500 MHz, DMSO-$D_6$):

δ: 11.41 (1H, br s), 10.41 (1H, br s), 8.26 (1H, t, J=1.6 Hz), 8.12 (2H, t, J=8.1 Hz), 8.03 (1H, dg, J=7.9, 0.9 Hz), 7.79-7.74 (38, m), 7.58 (21.4 d, J=8.5 Hz), 7.33 (1H, d, J=2.6 Hz), 7.20-7.14 (5H, m), 3.63-3.56 (1H, m), 3.24-3.16 (6H, m), 2.92-2.87 (4H, m), 2.79 (8H, s), 2.09-2.03 (1H, m), 1.84 (2H, d, J=11.9 Hz), 1.68-1.63 (4H, m), 1.58-1.53 (2H, m), 1.45-1.40 (4H, m), 1.34-1.25 (2H, m), 1.13 (3H, t, J=7.1 Hz)

Elemental analysis (measurement values): C: 63.60, H: 6.80, H: 9.56, O: 16.04, and S: 3.80

Measurement of Solubility:

Under shaking conditions at 37° C. for 30 minutes:

JP1: 1.4 µg/mL, JP2: 105.7 µg/mL, water: 31.7 µg/mL, Mc pH 6.0: 3.3 µg/mL

Under shaking conditions at 37° C. for 24 hours:

JP1: 1.4 µg/mL, JP2: 137.8 µg/mL, water: 429.5 µg/mL, Mc pH 6.0: 0.2 µg/mL

Reference Example 1

4-[2-(4-{[2-({3-[(trans-4-Carboxycyclohexyl)(ethyl)sulfamoyl]benzoyl}amino)-5-(piperidin-1-yl)benzoyl]amino}phenyl)ethyl]benzoic acid (1a) Methyl 4-(2-{4-[(5-fluoro-2-nitrobenzoyl)amino]phenyl}ethyl)benzoate

[Formula 15]

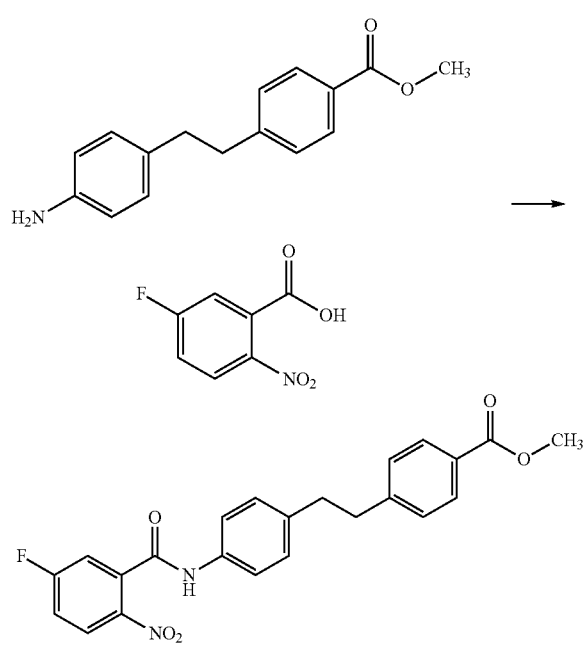

WSC (5.74 g) was added to a DCM (70 mL) suspension of 5-fluoro-2-nitrobenzoic acid (4.07 g) and methyl 4-[2-(4-aminophenyl)ethyl]benzoate (CAS registry number: 1346136-01-3, WO2011136269) (5.10 g) at room temperature. The reaction mixture was stirred at room temperature for 1 hour, was then diluted with a saturated ammonium chloride solution, and was then extracted with ethyl acetate. The organic layer was washed with saturated sodium hydrogen carbonate and a saturated saline, and was then dried over sodium sulfate. The resultant was filtered and concentrated. The residue was purified by column chromatography, and the obtained solid was ground in diisopropyl ether. The resultant was collected by filtration, and was then dried under reduced pressure to obtain 6.70 g of the title compound (79%) in the form of a light yellow solid.

(1b) Methyl 4-[2-(4-{[2-nitro-5-(piperidin-1-yl)benzoyl]amino}phenyl)ethyl]benzoate

[Formula 16]

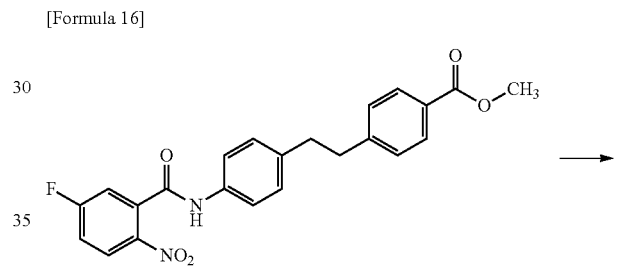

A solution of the compound (9.42 g) obtained in Reference Example (1a) and piperidine (6.6 mL) in THF (70 mL) was stirred at 50° C. for 3 hours. Thereafter, the reaction mixture was concentrated, was then stirred in water and ethyl acetate, and was then concentrated. The residue was ground in ethyl acetate/hexane, and was then collected by filtration. The resultant was dried under reduced pressure to obtain 10.3 g of the title compound (95%) is the form of a yellow solid.

$^1$H-NMR (400 MHz, CDCl$_3$) δ: 8.09 (1H, d, j=9.0 Hz), 7.95 (2H, d, J=8.2 Hz), 7.50 (2H, d, J=8.2 Hz), 7.31 (1H, s), 7.22 (2H, d, J=8.2 Hz), 7.13 (2H, d, J=8.2 Hz), 6.84-6.78 (2H, m), 3.91 (3H, s), 3.50-3.42 (4H, m), 3.00-2.87 (4H, m), 1.74-1.64 (6H, m).

(1c) Methyl 4-[2-(4-{[2-amino-5-(piperidin-1-yl)benzoyl]amino}phenyl)ethyl]benzoate

[Formula 17]

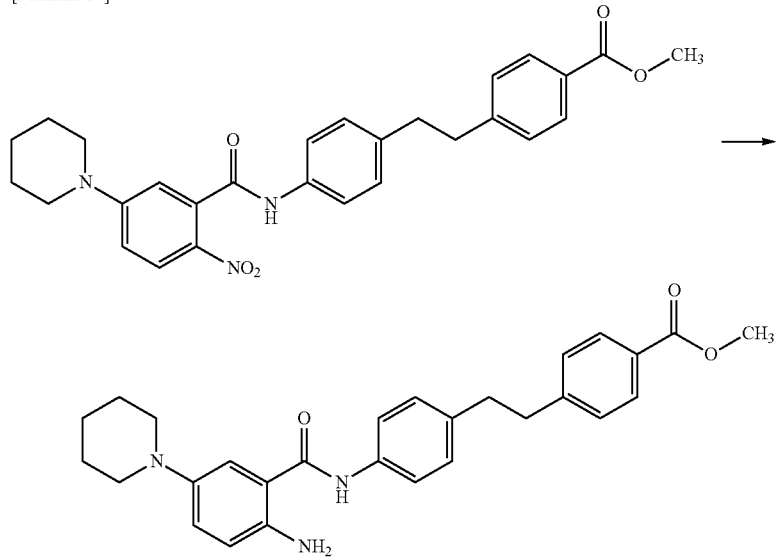

A suspension of the compound (10.3 g) obtained in Reference Example (1b) and palladium on carbon (10 wt %, 2.0 g) in THF/ethanol/methanol (1:1:1, 150 mL) was stirred under a hydrogen atmosphere at 50° C. for 4 hours. Thereafter, the reaction mixture was filtered with Celite, and was then concentrated. The residue was purified by column chromatography to obtain 9.30 g of the title compound (96%) in the form of a green amorphous substance.

$^1$H-NMR (400 MHz, CDCl$_3$) δ: 7.94 (2H, d, J=8.2 Hz), 7.91 (1H, s), 7.48 (2H, d, J=8.6 Hz), 7.22 (2H, d, J=8.6 Hz), 7.13 (2H, d, J=8.6 Hz), 7.10 (1H, d, J=2.7 Hz), 7.01 (1H, dd, J=8.6, 2.7 Hz), 6.70 (1H, d, J=8.6 Hz), 4.94 (2H, br s), 3.90 (3H, s), 3.02-2.90 (8H, m), 1.76-1.71 (4H, m), 1.58-1.52 (2H, m).

(1d) Methyl 4-{2-[4-({2-[(3-{ethyl[trans-4-(methoxycarbonyl)cyclohexyl]sulfamoyl}benzoyl)amino]-5-(piperidin-1-yl)benzoyl}amino)phenyl]ethyl}benzoate

[Formula 18]

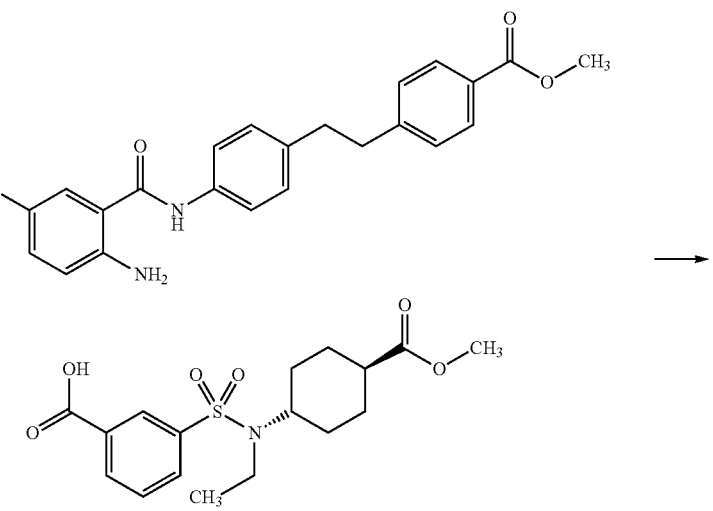

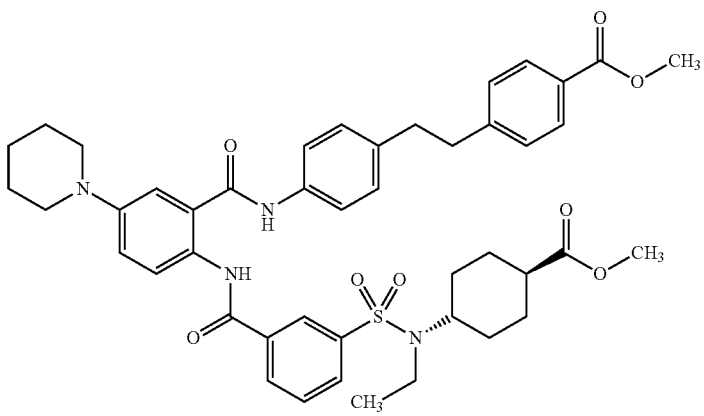

A solution of 3-{ethyl[trans-4-(methoxycarbonyl)cyclohexyl]sulfamoyl}benzoic acid (CAS registry number: 1346136-17-1, WO2011136269) (9.0 g), the compound (9.29 g) obtained in Reference Example (10), HBTU (15.4 g) and DIPEA (10.6 mL) in DMF (70 mL) was stirred at room temperature for 16 hours. Thereafter, the reaction mixture was diluted with water, and was then extracted with ethyl acetate. The organic layer was washed with a saturated saline, and was then dried over magnesium sulfate. The resultant was filtered and concentrated. The obtained solid was ground in ethyl acetate. The resultant was collected by filtration, and was then dried under reduced pressure to obtain 15.4 g of the title compound (94%) is the form of a yellow solid.

$^1$H-NMR (400 MHz, CDCl$_3$) δ: 11.54 (1H, s), 8.60 (1H, d, J=9.4 Hz), 8.44 (1H, s), 8.12 (1H, d, J=8.2 Hz), 7.99 (1H, d, J=7.8 Hz), 7.95 (2H, d, J=8.2 Hz), 7.88 (1H, s), 7.61 (1H, t, J=7.8 Hz), 7.49 (2H, d, J=8.2 Hz), 7.23 (2H, d, J=8.2 Hz), 7.19-7.14 (4H, m), 3.91 (3H, s), 3.69-3.64 (1H, m), 3.63 (3H, s), 3.29 (2H, q, J=7.0 Hz), 3.16 (4H, t, J=5.5 Hz), 3.00-2.93 (4H, m), 2.18-2.08 (1H, m), 2.02-1.94 (2H, m), 1.78-1.69 (6H, m), 1.64-1.58 (2H, m), 1.50-1.40 (4H, m), 1.25 t, J=7.2 Hz).

(1e) 4-[2-(4-{[2-({3-[(trans-4-Carboxycyclohexyl)(ethyl)sulfamoyl]benzoyl}amino)-5-(piperidin-1-yl)benzoyl]amino}phenyl)ethyl]benzoic acid

[Formula 19]

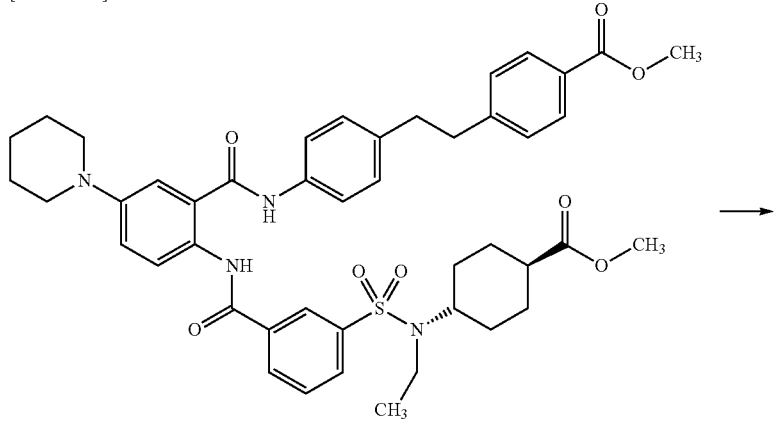

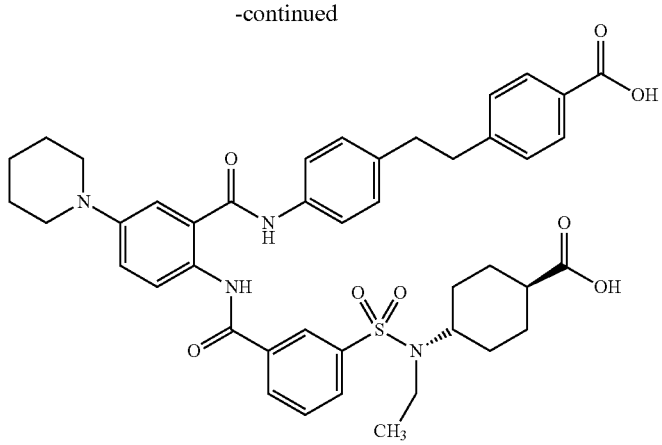

A 5 N NaOH aqueous solution (19 mL) was added to a suspension of the compound (15.4 g) obtained in Reference Example (1d) in THF/methanol (1:2, 150 mL) at room temperature. The reaction mixture was heated to 50° C., and was then stirred for 5 hours. Thereafter, the reaction mixture was cooled to room temperature, and 1 N HCl was then added to the mixture (in an amount in which the reaction mixture became cloudy). The obtained mixture was diluted with water, and was then extracted with ethyl acetate. The organic layer was washed with a saturated saline, and was then dried over sodium sulfate. The resultant was filtered and was then concentrated. The residue was purified by column chromatography, and thereafter, the obtained solid was ground in ethyl acetate, was then collected by filtration, and was dried under reduced pressure to obtain 14.7 g of the title compound (98%) in the form of a yellow solid.

$^1$H-NMR (400 MHz, DMSO-D$_6$) δ: 11.38 (1H, s), 10.39 (1H, s), 8.27 (1H, s), 8.15-8.08 (2H, m), 8.04 (1H, d, J=7.4 Hz), 7.84 (2H, d, J=8.2 Hz), 7.76 (1H, t, j=7.8 Hz), 7.59 (2H, d, J=8.6 Hz), 7.34 (3H, d, J=8.2 Hz), 7.18 (3H, d, J=8.2 Hz), 3.66-3.55 (1H, m), 3.25-3.18 (6H, m), 2.98-2.85 (4H, m), 2.12-2.03 (1H, m), 1.84 (2H, br d, J=12.1 Hz), 1.70-1.62 (4H, m), 1.60-1.52 (2H, m), 1.51-1.41 (4H, m), 1.38-1.25 (2H, m), 1.13 (3H, t, J=7.0 Hz).

MS(ESI) m/z: 781 (M+H)$^+$.

The invention claimed is:

1. Crystals of a salt, or hydrate thereof, of a compound of formula (I):

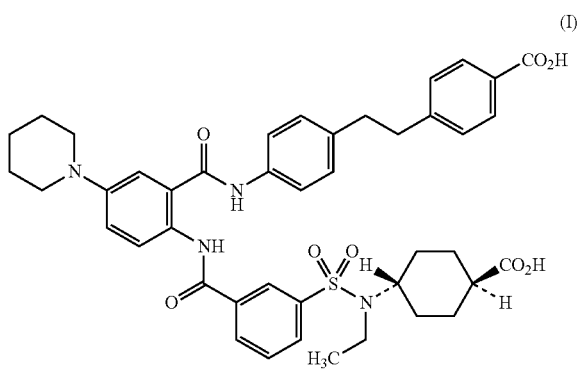

wherein the crystals are α crystals, β crystals, γ crystals, or δ crystals.

2. The crystals of a salt, or hydrate thereof, of a compound according to claim 1, wherein the salt is a disodium salt.

3. The crystals of a salt, or hydrate thereof, of a compound according to claim 1, wherein the hydrate is a trihydrate.

4. Crystals of a disodium salt trihydrate of the compound of formula (I):

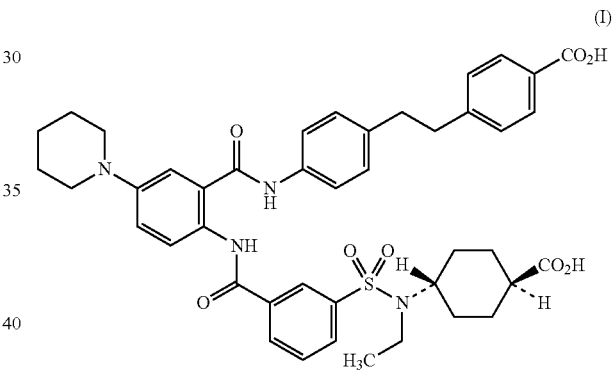

wherein the crystals are α crystals.

5. The crystals according to claim 4, wherein the crystals are α crystals, and wherein, in powder X-ray diffractometry using Cu as a radiation source, 2θ(°) shows peaks at around 5.72, around 10.10, around 10.96, around 11.98, around 13.34, around 15.02, around 17.26, around 20.26, around 21.66, and around 22.36.

6. The crystals or hydrates thereof according to claim 2, wherein the crystals are β crystals, and wherein, in powder X-ray diffractometry using Cu as a radiation source, 2θ(°) shows peaks at around 5.82, around 9.78, around 11.18, around 12.26, around 12.86, around 15.38, around 16.34, around 18.34, around 19.68, and around 22.54.

7. The crystals or hydrates thereof according to claim 2, wherein the crystals are γ crystals, and wherein, in powder X-ray diffractometry using Cu as a radiation source, 2θ(°) shows peaks at around 5.80, around 9.86, around 12.12, around 12.86, around 15.04, around 16.30, around 18.28, around 19.90, around 20.52, and around 22.58.

8. The crystals or hydrates thereof according to claim 2, wherein the crystals are δ crystals, and wherein, in powder X-ray diffractometry using Cu as a radiation source, 2θ(°) shows a single characteristic peak only at around 6.04.

9. A pharmaceutical composition comprising the crystals or hydrates thereof according to claim 1.

10. The pharmaceutical composition according to claim 9, wherein the composition inhibits phosphorus uptake.

11. A method of treating hyperphosphatemia in a subject comprising, administering to a subject in need thereof the pharmaceutical composition according to claim 9.

12. A method of treating hyperphosphatemia in a subject comprising, administering to a subject in need thereof the crystals according to claim 1.

13. A method for preventing or treating hyperphosphatemia, comprising administering to a subject an effective amount of the crystals or hydrates thereof according to claim 1.

* * * * *